(12) United States Patent
Kim et al.

(10) Patent No.: US 10,098,609 B2
(45) Date of Patent: Oct. 16, 2018

(54) X RAY APPARATUS AND METHOD OF OPERATING THE SAME

(71) Applicant: SAMSUNG ELECTRONICS CO., LTD., Suwon-si (KR)

(72) Inventors: Tae-eui Kim, Seongnam-si (KR);
Do-hyeong Hwang, Gunpo-si (KR);
Seung-hoon Kim, Suwon-si (KR);
Sung-jin Park, Suwon-si (KR);
Il-hwan Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/965,945

(22) Filed: Dec. 11, 2015

(65) Prior Publication Data

US 2016/0166230 A1 Jun. 16, 2016

(30) Foreign Application Priority Data

Dec. 12, 2014 (KR) .................. 10-2014-0179811
Jul. 20, 2015 (KR) .................. 10-2015-0102409
Nov. 30, 2015 (KR) .................. 10-2015-0169287

(51) Int. Cl.
*A61B 6/12* (2006.01)
*A61B 6/00* (2006.01)
(Continued)

(52) U.S. Cl.
CPC ............... *A61B 6/587* (2013.01); *A61B 6/06* (2013.01); *A61B 6/4464* (2013.01); *A61B 6/465* (2013.01); *A61B 6/588* (2013.01); *G01N 23/04* (2013.01); *A61B 6/467* (2013.01); *G01N 2223/308* (2013.01); *G01N 2223/32* (2013.01); *G01N 2223/41* (2013.01); *G01N 2223/419* (2013.01); *G01N 2223/427* (2013.01); *G01N 2223/612* (2013.01)

(58) Field of Classification Search
CPC .......... A61B 6/587; A61B 6/08; A61B 6/547; A61B 6/4405; A61B 6/4441
USPC ....................................... 378/205
See application file for complete search history.

(56) References Cited

U.S. PATENT DOCUMENTS 7,156,553 B2  1/2007  Tanaka et al.
8,690,426 B2  4/2014  Liu et al.
(Continued)

FOREIGN PATENT DOCUMENTS

EP   1245188 A2   10/2002
JP   3-251231 A   11/1991
(Continued)

OTHER PUBLICATIONS

Communication dated May 2, 2016 issued by the European Patent Office in counterpart European Patent Application No. 15199561.0.
(Continued)

*Primary Examiner* — Don Wong
(74) *Attorney, Agent, or Firm* — Sughrue Mion, PLLC

(57) ABSTRACT

An X-ray apparatus which aligns an X-ray radiator with an X-ray detector, an X-ray apparatus which aligns an X-ray radiator with an X-ray detector while maintaining a Source to Image-receptor Distance (SID) and a Source to Object Distance (SOD) therebetween, and methods of operating the X-ray apparatuses are provided.

19 Claims, 20 Drawing Sheets

(51) Int. Cl.
*G01N 23/04* (2018.01)
*A61B 6/06* (2006.01)

(56) References Cited

U.S. PATENT DOCUMENTS

| | | |
|---|---|---|
| 9,155,509 B2 | 10/2015 | Lalena et al. |
| 2003/0103597 A1 | 6/2003 | Sklebitz |
| 2005/0069091 A1 | 3/2005 | Arakawa |
| 2008/0285723 A1 | 11/2008 | Lumma et al. |
| 2014/0247918 A1* | 9/2014 | Kang .................. A61B 6/4452 378/62 |

FOREIGN PATENT DOCUMENTS

| | | |
|---|---|---|
| JP | 2000-23955 A | 1/2000 |
| JP | 2010-119485 A | 6/2010 |
| JP | 2011-4869 A | 1/2011 |
| KR | 10-2013-0057991 A | 6/2013 |
| KR | 10-2014-0108989 A | 9/2014 |
| WO | 2013162762 A1 | 10/2013 |

OTHER PUBLICATIONS

Communication dated Feb. 16, 2018 by the European Patent Office in counterpart European Patent Application No. 15199561.0.

\* cited by examiner

X RAY APPARATUS AND METHOD OF OPERATING THE SAME

CROSS-REFERENCE TO RELATED PATENT APPLICATIONS

This application claims priority to Korean Patent Application No. 10-2014-0179811, filed on Dec. 12, 2014, Korean Patent Application No. 10-2015-0102409, filed on Jul. 20, 2015, and Korean Patent Application No. 10-2015-0169287, filed on Nov. 30, 2015 in the Korean Intellectual Property Office, the disclosures of which are incorporated herein in their entirety by reference.

BACKGROUND

1. Field

Apparatuses and methods consistent with the present disclosure relate to an X-ray apparatus and a method of operating the X-ray apparatus.

2. Description of the Related Art

In general, X-rays are electromagnetic waves having a wavelength of 0.01 to 100 nm and can pass through an object. Thus, they may be commonly used in a wide range of applications, such as medical equipment that take images of the inside of a living body and non-destructive testing equipment for industrial use.

X-ray photographing apparatuses using X-rays allow X-rays emitted by an X-ray source to pass through an object, and detect a difference between the intensities of the passed X-rays from an X-ray detector to thereby acquire an X-ray image of the object. X-ray imaging apparatuses are able to easily identify the internal structure of an object based on an X-ray image of the object and to diagnose a disease of the object. X-ray apparatuses are able to easily identify the internal structure of an object by using the principle that the transmission coefficient of X-rays varies depending on the density of the object and the atomic number of an atom of the object. As the wavelength of an X-ray becomes shorter, the transmission coefficient of X-rays increases, and a picture on a screen becomes clearer.

SUMMARY

Provided are X-ray apparatuses and detectors capable of easily performing X-ray photography.

Additional aspects will be set forth in part in the description which follows and, in part, will be apparent from the description, or may be learned by practice of the presented exemplary embodiments.

According to an aspect of an exemplary embodiment, an X-ray apparatus includes an X-ray radiator; an X-ray detector; a driving controller configured to acquire first angle information representing an inclination of the X-ray detector, and second angle information representing an angle by which the X-ray radiator has been rotated in a predetermined direction, and to determine a rotation angle and a rotation direction for aligning the X-ray radiator with the X-ray detector, based on the first angle information and the second angle information; and a driver configured to rotate the X-ray radiator by the rotation angle in the rotation direction.

The first angle information may include a first angle representing an inclination of an incidence surface of the X-ray detector. The second angle information may include a second angle representing an angle by which the X-ray radiator has been rotated in the predetermined direction. The driving controller may determine the rotation angle, based on a difference between the first angle and the second angle, and determine the predetermined direction to be the rotation direction.

The X-ray apparatus may further include an output unit configured to, when the X-ray radiator rotates by the rotation angle in the rotation direction, display, on a screen of the output unit, information representing that the X-ray radiator is aligned with the X-ray detector.

The output unit may further display the first angle information and the second angle information.

The X-ray apparatus may further include a user input unit configured to receive a command regarding alignment of the X-ray radiator with the X-ray detector from a user. The driving controller may determine the rotation angle and the rotation direction according to the command, and the driver may rotate the X-ray radiator by the rotation angle in the rotation direction.

The driving controller may transmit the rotation angle and the rotation direction to the driver via a Controller Area Network (CAN).

According to an aspect of an exemplary embodiment, a method of operating an X-ray apparatus includes acquiring first angle information representing an inclination of an X-ray detector, and second angle information representing an angle by which an X-ray radiator is rotated in a predetermined direction; determining a rotation angle and a rotation direction for aligning the X-ray radiator with the X-ray detector, based on the first angle information and the second angle information; and rotating the X-ray radiator by the rotation angle in the rotation direction.

According to an aspect of an exemplary embodiment, an X-ray apparatus includes an X-ray radiator; an X-ray detector; a driving controller configured to acquire motion information representing that the X-ray detector is rotated in a predetermined direction by a predetermined angle, and to determine a rotation angle and a rotation direction for aligning the X-ray radiator with the X-ray detector, based on the acquired motion information; and a driver configured to rotate the X-ray radiator by the rotation angle determined based on the motion information, in the rotation direction determined based on the motion information.

The driving controller may determine the predetermined angle to be the rotation angle and determine the predetermined direction to be the rotation direction.

According to an aspect of an exemplary embodiment, a method of operating an X-ray apparatus includes acquiring motion information representing that an X-ray detector is rotated in a predetermined direction by a predetermined angle; determining a rotation angle and a rotation direction for aligning an X-ray radiator with the X-ray detector, based on the acquired motion information; and rotating the X-ray radiator by the rotation angle determined based on the motion information, in the rotation direction determined based on the motion information.

According to an aspect of an exemplary embodiment, an X-ray apparatus includes an X-ray radiator; an X-ray detector; a driving controller configured to acquire angle information representing an inclination of the X-ray detector, information about a preset point on the X-ray detector, and information about a Source to Image-receptor Distance (SID) which is a distance between the preset point and the X-ray radiator, and to determine a location and a rotation angle for aligning the X-ray radiator with the X-ray detector while maintaining the SID, based on the acquired pieces of information; and a driver configured to move and rotate the X-ray radiator according to the location and the rotation angle.

The X-ray apparatus may further include an image acquirer configured to acquire an image of the X-ray detector.

The driving controller may acquire information about the SID, based on the image.

The driving controller may detect a marker displayed on the X-ray detector from the image by using a collimator, and acquire information about the SID.

The marker may be an intersection between cross lines of the collimator that is marked on the X-ray detector when a lamp of the collimator is turned on, or may be an intersection between the cross lines of the collimator that is marked by a laser pointer included in the collimator.

The driving controller may further acquire information about a preset point on an object located between the X-ray radiator and the X-ray detector and information about a Source to Object Distance (SOD) which is a distance between the preset point on the object and the X-ray radiator, and determine a location and a rotation angle for aligning the X-ray radiator with the X-ray detector while maintaining the SOD, based on the acquired pieces of information. The driver may move and rotate the X-ray radiator according to the location and rotation angle determined to maintain the SOD and align the X-ray radiator with the X-ray detector.

According to an aspect of an exemplary embodiment, a method of operating an X-ray apparatus includes acquiring angle information representing an inclination of an X-ray detector, information about a preset point on the X-ray detector, and information about an SID which is a distance between the preset point on the X-ray detector and the X-ray radiator; determining a location and a rotation angle for aligning the X-ray radiator with the X-ray detector while maintaining the SID, based on the acquired pieces of information; and moving and rotating the X-ray radiator according to the location and the rotation angle.

According to an aspect of an exemplary embodiment, a non-transitory computer-readable recording medium has recorded thereon a computer program, which, when executed by a computer, performs the methods.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
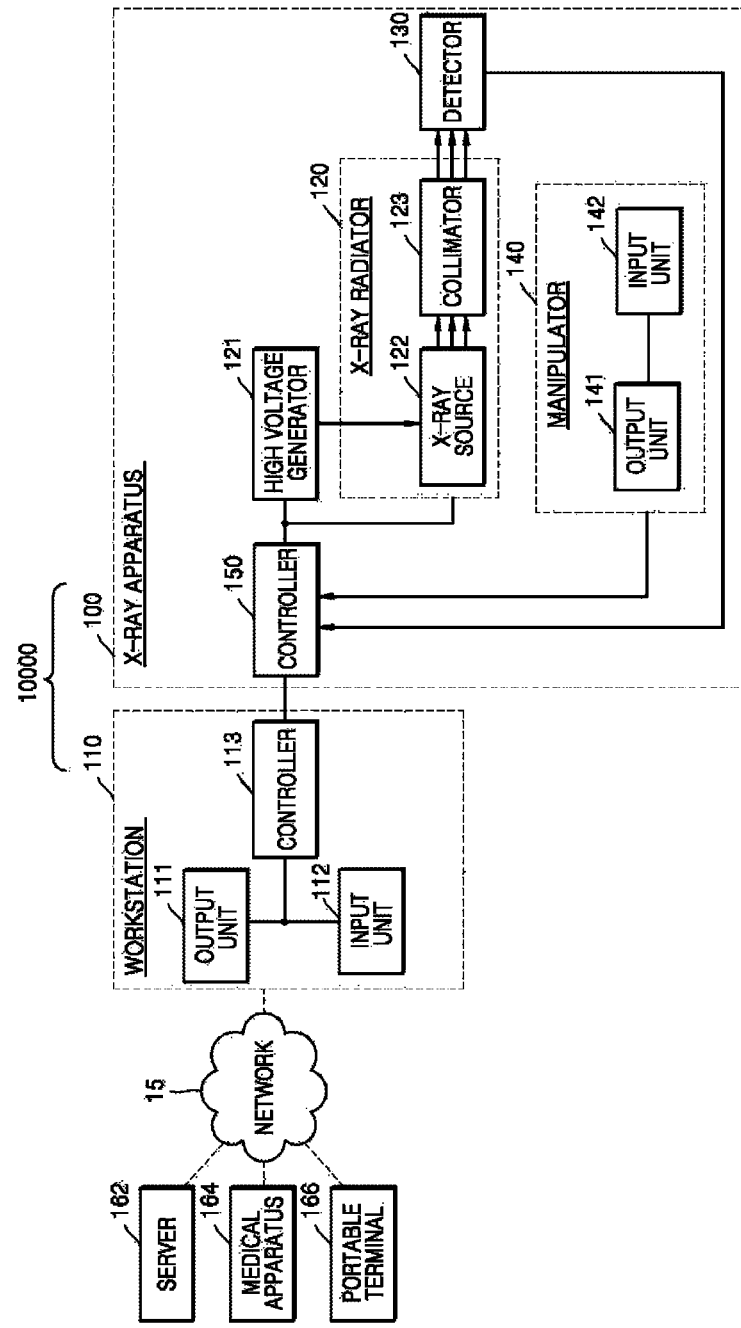
FIG. 1 is a block diagram of an X-ray system.

The attached drawings for illustrating exemplary embodiments of the present disclosure are referred to in order to gain a sufficient understanding of the present disclosure, the merits thereof, and the objectives accomplished by the implementation of the present disclosure. In this regard, the exemplary embodiments may have different forms and should not be construed as being limited to the descriptions set forth herein. Rather, these exemplary embodiments are provided so that this disclosure will be thorough and complete and will fully convey the concepts of the exemplary embodiments to one of ordinary skill in the art, and the present disclosure will only be defined by the appended claims.

Hereinafter, the terms used in the specification will be briefly described, and then the present disclosure will be described in detail.

The terms used in this specification are those general terms currently widely used in the art in consideration of functions regarding the present disclosure, but the terms may vary according to the intention of those of ordinary skill in the art, precedents, or new technology in the art. Also, some terms may be selected by the applicant, and in this case, the meaning of the selected terms will be described in detail in the detailed description of the present specification. Thus, the terms used in the specification should be understood not as simple names but based on the meaning of the terms and the overall description of the exemplary embodiment.

Throughout the specification, an "image" may denote multi-dimensional data composed of discrete image elements (for example, pixels in a two-dimensional image and voxels in a three-dimensional image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

Furthermore, in the present specification, an "object" may be a human, an animal, or a part of a human or animal. For example, the object may include an organ (for example, the liver, the heart, the womb, the brain, breasts, or the abdomen), blood vessels, or a combination thereof. Throughout the specification, a "user" may be, but is not limited to, a medical expert, for example, a medical doctor, a nurse, a medical laboratory technologist, or a medical imaging expert, or a technician who repairs medical apparatuses.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest photographing, simple abdomen photographing, simple skeleton photographing, simple nasal sinuses photographing, simple neck soft tissue photographing, and breast photographing.

FIG. 1 is a block diagram of an X-ray system 10000.

Referring to FIG. 1, the X-ray system 10000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray radiator 120, a high voltage generator 121, a detector 130, a manipulator 140, and a controller 150. The controller 150 may control overall operations of the X-ray apparatus 100.

The high voltage generator 121 generates a high voltage for generating X-rays, and applies the high voltage to an X-ray source 122.

The X-ray radiator 120 includes the X-ray source 122 receiving the high voltage from the high voltage generator 121 to generate and radiate X-rays, and a collimator 123 for guiding a path of the X-ray radiated from the X-ray source 122 and adjusting an irradiation region radiated by the X-ray.

The X-ray source 122 includes an X-ray tube that may be realized as a vacuum tube diode including a cathode and an anode.

The detector 130 detects an X-ray that is radiated from the X-ray radiator 120 and has been transmitted through an object. The detector 130 may be a digital detector. The detector 130 may be implemented by using a thin film transistor (TFT) or a charge coupled device (CCD). Although the detector 130 is included in the X-ray apparatus 100 in FIG. 1, the detector 130 may be an X-ray detector that is a separate device capable of being connected to or separated from the X-ray apparatus 100.

The X-ray apparatus 100 may further include a manipulator 140 for providing a user with an interface for manipulating the X-ray apparatus 100. The manipulator 140 may include an output unit 141 and an input unit 142. The input unit 142 may receive from a user a command for manipulating the X-ray apparatus 100 and various types of information related to X-ray photographing. The controller 150 may control or manipulate the X-ray apparatus 100 according to the information received by the input unit 142. The output unit 141 may output sound representing information related to a photographing operation such as the X-ray radiation under the control of the controller 150.

The workstation 110 and the X-ray apparatus 100 may be connected to each other by wire or wirelessly. When they are connected to each other wirelessly, a device (not shown) for synchronizing clock signals with each other may be further included. The workstation 110 and the X-ray apparatus 100 may exist within physically separate spaces.

The workstation 110 may include an output unit 111, an input unit 112, and a controller 113. The output unit 111 and the input unit 112 provide a user with an interface for manipulating the workstation 110 and the X-ray apparatus 100. The controller 113 may control the workstation 110 and the X-ray apparatus 100.

The X-ray apparatus 100 may be controlled via the workstation 110 or may be controlled by the controller 150 included in the X-ray apparatus 100. Accordingly, a user may control the X-ray apparatus 100 via the workstation 110 or may control the X-ray apparatus 100 via the manipulator 140 and the controller 150 included in the X-ray apparatus 100. In other words, a user may remotely control the X-ray apparatus 100 via the workstation 110 or may directly control the X-ray apparatus 100.

Although the controller 113 of the workstation 110 is separate from the controller 150 of the X-ray apparatus 100 in FIG. 1, FIG. 1 is only an example. As another example, the controllers 113 and 150 may be integrated into a single controller, and the single controller may be included in only one of the workstation 110 and the X-ray apparatus 100. Hereinafter, the controllers 113 and 150 may denote the controller 113 of the workstation 110 and/or the controller 150 of the X-ray apparatus 100.

The output unit 111 and the input unit 112 of the workstation 110 may provide a user with an interface for manipulating the workstation 110, and the output unit 141 and the input unit 142 of the X-ray apparatus 100 may also provide a user with an interface for manipulating the X-ray apparatus 100. Although the workstation 110 and the X-ray radiation apparatus 100 include the output units 111 and 141, respectively, and the input units 112 and 142, respectively, in FIG. 1, exemplary embodiments are not limited thereto. Only one of the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include a keyboard, a mouse, a touch screen, a voice recognizer, a fingerprint recognizer, an iris recognizer, and other input devices which are well known to one of ordinary skill in the art. The user may input a command for radiating the X-ray via the input units 112 and 142, and the input units 112 and 142 may include a switch for inputting the command. The switch may be configured so that a radiation command for radiating the X-ray may be input only when the switch is pushed in two steps.

In other words, when the user pushes the switch, a prepare command for performing a pre-heating operation for X-ray radiation may be input, and in this state, when the user pushes the switch deeper, a radiation command for performing substantial X-ray radiation may be input. When the user manipulates the switch as described above, the controllers 113 and 150 generate signals corresponding to the commands input through the switch manipulation, that is, a prepare signal, and transmit the generated signals to the high voltage generator 121 generating a high voltage for generating the X-ray.

When the high voltage generator 121 receives the prepare signal from the controllers 113 and 150, the high voltage generator 121 starts a pre-heating operation, and when the pre-heating is finished, the high voltage generator 121 outputs a ready signal to the controllers 113 and 150. In addition, the detector 130 also needs to prepare to detect the X-ray, and thus the high voltage generator 121 performs the pre-heating operation and the controllers 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 outputs a ready signal to the controllers 113 and 150.

When the pre-heating operation of the high voltage generator 121 is finished and the detector 130 is ready to detect the X-ray, the controllers 113 and 150 transmit a radiation signal to the high voltage generator 121, the high voltage generator 121 generates and applies the high voltage to the X-ray source 122, and the X-ray source 122 radiates the X-ray.

The controllers 113 and 150 control locations of the X-ray radiator 120 and the detector 130, photographing timing, and photographing conditions, according to photographing conditions set by the user.

In more detail, the controllers 113 and 150 control the high voltage generator 121 and the detector 130 according to the command input via the input units 112 and 142 so as to control radiation timing of the X-ray, an intensity of the X-ray, and a region radiated by the X-ray. In addition, the controllers 113 and 150 adjust the location of the detector 130 according to a predetermined photographing condition, and controls operation timing of the detector 130.

Furthermore, the controllers 113 and 150 generate a medical image of the object by using image data received via the detector 130. In detail, the controllers 113 and 150 may receive the image data from the detector 130, and then, generate the medical image of the object by removing noise from the image data.

The output units 111 and 141 may output the medical image generated by the controllers 113 and 150. The output units 111 and 141 may output information that is necessary for the user to manipulate the X-ray apparatus 100, for example, a user interface (UI), user information, or object information. Examples of the output units 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

The workstation 110 shown in FIG. 1 may further include a communicator (not shown) that may be connected to a server 162, a medical apparatus 164, and a portable terminal 166 via a network 15.

The communicator may be connected to the network 15 by wire or wirelessly to communicate with the server 162, the medical apparatus 164, or the portable terminal 166. The communicator may transmit or receive data related to diagnosis of the object via the network 15, and may also transmit or receive medical images captured by the medical apparatus 164, for example, a CT apparatus, an MRI apparatus, or an X-ray apparatus. Moreover, the communicator may receive a medical history or treatment schedule of an object (e.g., a patient) from the server 162 to diagnose a disease of the object. Also, the communicator may perform data communication with the portable terminal 166 such as a mobile phone, a personal digital assistant (PDA), or a laptop computer of a medical doctor or a client, as well as the server 162 or the medical apparatus 164 in a hospital.

The communicator may include one or more elements enabling communication with external apparatuses. For example, the communicator may include a local area communication module, a wired communication module, and a wireless communication module.

The local area communication module refers to a module for performing local area communication with an apparatus located within a predetermined distance. Examples of local area communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module refers to a module for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include a plurality of digital signal processors (DSPs), an ultra-small calculator, and a processing circuit for special purposes (for example, high speed analog/digital (A/D) conversion, high speed Fourier transformation, and an array process).

In addition, communication between the workstation 110 and the X-ray apparatus 100 may be performed using a high speed digital interface, such as low voltage differential signaling (LVDS), asynchronous serial communication, such as a universal asynchronous receiver transmitter (UART), a low latency network protocol, such as error synchronous serial communication or a controller area network (CAN), or any of other various communication methods that are well known to one of ordinary skill in the art.

Figure 2:
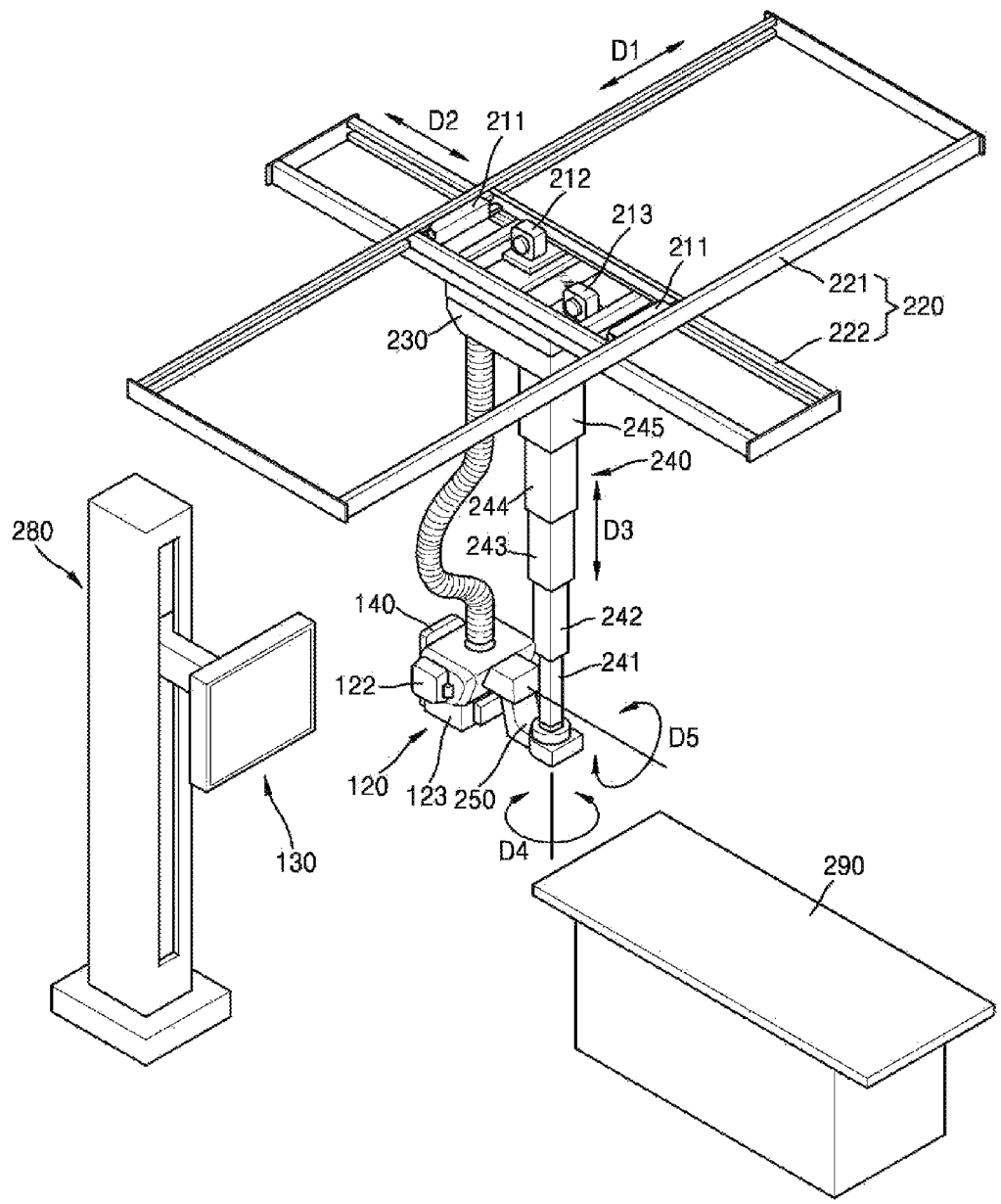
FIG. 2 is a perspective view of a fixed type X-ray apparatus.

FIG. 2 is a perspective view of a fixed type X-ray apparatus 200. The fixed type X-ray apparatus 200 may be another exemplary embodiment of the X-ray apparatus 100 of FIG. 1. Components included in the fixed type X-ray apparatus 200 that are the same as those of the X-ray apparatus 100 of FIG. 1 use the same reference numerals, and repeated descriptions thereof will be omitted.

Referring to FIG. 2, the fixed type X-ray apparatus 200 includes a manipulator 140 providing a user with an interface for manipulating the X-ray apparatus 200, an X-ray radiator 120 radiating an X-ray to an object, a detector 130 detecting an X-ray that has passed through the object, first, second, and third motors 211, 212, and 213 providing a driving power to transport the X-ray radiator 120, a guide rail 220, a moving carriage 230, and a post frame 240. The guide rail 220, the moving carriage 230, and the post frame 240 are formed to transport the X-ray radiator 120 by using the driving power of the first, second, and third motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other at 90°.

The first guide rail 221 is provided on the ceiling of an examination room in which the X-ray apparatus 200 is disposed.

The second guide rail 222 is located under the first guide rail 221, and is mounted so as to slide along the first guide rail 221. A roller (not shown) that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90°, and may be parallel to the ceiling of the examination room.

The moving carriage 230 is disposed under the second guide rail 222 so as to move along the second guide rail 222. A roller (not shown) moving along the second guide rail 222 may be provided on the moving carriage 230.

Therefore, the moving carriage 230 may move in the first direction D1 together with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be foldable, and thus, the post frame 240 may have a length that is adjustable in a vertical direction of the examination room while in a state of being fixed to the moving carriage 230.

A third direction D3 is defined as a direction in which the length of the post frame 240 increases or decreases. Therefore, the third direction D3 may be perpendicular to the first direction D1 and the second direction D2.

The detector 130 detects the X-ray that has passed through the object, and may be combined with a table 290 or a stand 280.

A rotating joint 250 is disposed between the X-ray radiator 120 and the post frame 240. The rotating joint 250 allows the X-ray radiator 120 to be coupled to the post frame 240, and supports a load applied to the X-ray radiator 120.

The X-ray radiator 120 connected to the rotating joint 250 may rotate on a plane that is perpendicular to the third direction D3. In this case, a rotating direction of the X-ray radiator 120 may be defined as a fourth direction D4.

Also, the X-ray radiator 120 may be configured to be rotatable on a plane perpendicular to the ceiling of the examination room. Therefore, the X-ray radiator 120 may rotate in a fifth direction D5 that is a rotating direction about an axis that is parallel with the first direction D1 or the second direction D2, with respect to the rotating joint 250.

The first, second, and third motors 211, 212, and 213 may be provided to move the X-ray radiator 120 in the first, second, and third directions D1, D2, and D3. The first, second, and third motors 211, 212, and 213 may be electrically driven, and the first, second, and third motors 211, 212, and 213 may respectively include an encoder.

The first, second, and third motors 211, 212, and 213 may be disposed at various locations in consideration of design convenience. For example, the first motor 211, moving the second guide rail 222 in the first direction D1, may be disposed around the first guide rail 221, the second motor 212, moving the moving carriage 230 in the second direction D2, may be disposed around the second guide rail 222, and the third motor 213, increasing or reducing the length of the post frame 240 in the third direction D3, may be disposed in the moving carriage 230. In another example, the first, second, and third motors 211, 212, and 213 may be connected to a driving power transfer unit (not shown) so as to linearly move the X-ray radiator 120 in the first, second, and third directions D1, D2, and D3. The driving power transfer unit may be a combination of a belt and a pulley, a combination of a chain and a sprocket, or a shaft, which are generally used.

In another example, motors (not shown) may be disposed between the rotating joint 250 and the post frame 240 and between the rotating joint 250 and the X-ray radiator 120 in order to rotate the X-ray radiator 120 in the fourth and fifth directions D4 and D5.

The manipulator 140 may be disposed on a side surface of the X-ray radiator 120.

FIG. 2 shows the fixed type X-ray apparatus 200 connected to the ceiling of the examination room. However, the fixed type X-ray apparatus 200 is merely an example for convenience of comprehension. That is, X-ray apparatuses according to exemplary embodiments of the present disclosure may include X-ray apparatuses having various structures that are well known to one of ordinary skill in the art, for example, a C-arm-type X-ray apparatus and an angiography X-ray apparatus, in addition to the fixed type X-ray apparatus 200 of FIG. 2.

Figure 3:
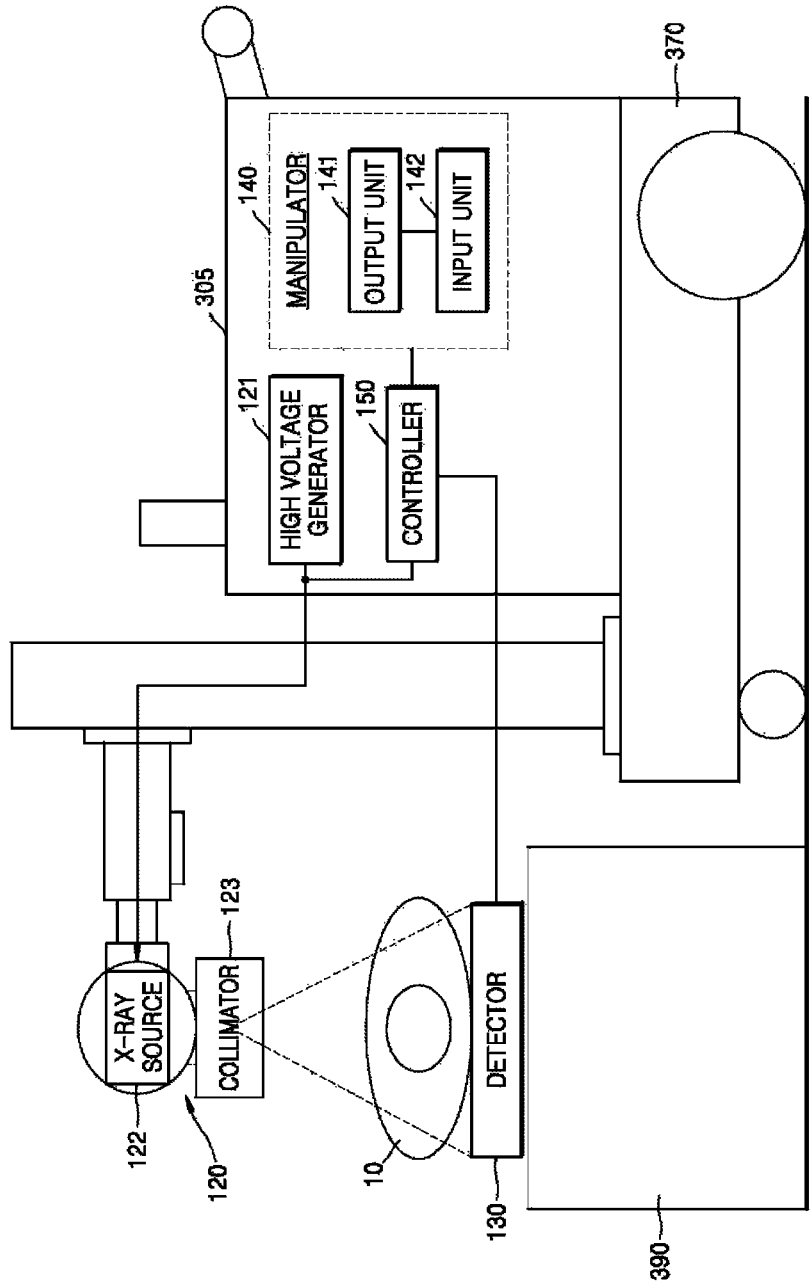
FIG. 3 is a block diagram of a mobile X-ray apparatus.

FIG. 3 is a diagram showing a configuration of a mobile X-ray apparatus 300 capable of performing an X-ray photographing operation regardless of the location where the photographing operation is performed. The mobile X-ray apparatus 300 may be another exemplary embodiment of the X-ray apparatus 100 of FIG. 1. Components included in the mobile X-ray apparatus 300 that are the same as those of the X-ray apparatus 100 of FIG. 1 use the same reference numerals as those used in FIG. 1, and a repeated description thereof will be omitted.

Referring to FIG. 3, the mobile X-ray apparatus 300 includes a transport unit 370 including a wheel for transporting the mobile X-ray apparatus 300, a main unit 305, an X-ray radiator 120, and a detector 130 detecting an X-ray that is radiated from the X-ray radiator 120 toward an object 10 and transmitted through the object 10 on a table 390. The main unit 305 includes a manipulator 140 providing a user with an interface for manipulating the mobile X-ray apparatus 300, a high voltage generator 121 generating a high voltage applied to an X-ray source 122, and a controller 150 controlling overall operations of the mobile X-ray apparatus 300. The X-ray radiator 120 includes the X-ray source 122 generating the X-ray, and a collimator 123 guiding a path along which the generated X-ray is emitted from the X-ray source 122 and adjusting an irradiation region radiated by the X-ray.

The detector 130 in FIG. 3 may be separate from the table 390. In other words, the detector 130 may be a portable detector which can exist anywhere.

In FIG. 3, the manipulator 140 is included in the main unit 305; however, exemplary embodiments are not limited thereto. For example, as illustrated in FIG. 2, the manipulator 140 of the mobile X-ray apparatus 300 may be disposed on a side surface of the X-ray radiator 120.

Figure 4:
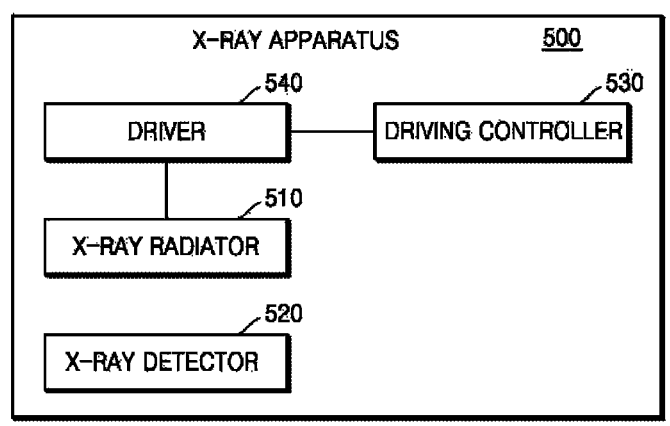
FIG. 4 is a block diagram of an X-ray apparatus according to an exemplary embodiment.

FIG. 4 is a block diagram of an X-ray apparatus 500 according to an exemplary embodiment.

The X-ray apparatus 500 may include an X-ray detector 520, an X-ray radiator 510, a driving controller 530, and a driver 540. Only components related with the present exemplary embodiment from among the components of the X-ray apparatus 500 are shown in FIG. 4. It will be understood by one of ordinary skill in the art that general-use components other than the components illustrated in FIG. 4 may be further included.

Since the X-ray radiator 510 may include the features of the X-ray radiator 120 of FIGS. 1-3, a redundant description thereof will be omitted here. Since the X-ray detector 520 may include the features of the X-ray detector 130 of FIGS. 1-3, a redundant description thereof will be omitted here.

The driving controller 530 may acquire first angle information representing an inclination of the X-ray detector 520, and second angle information representing an angle by which the X-ray radiator 510 has been rotated in a predetermined direction, and determine a rotation angle and a rotation direction for aligning the X-ray radiator 510 with the X-ray detector 520, based on the first angle information and the second angle information. The alignment of the X-ray radiator 510 with the X-ray detector 520 may denote that the X-ray radiator 510 radiates an X-ray in a direction perpendicular to an incidence surface of the X-ray detector 520.

According to an exemplary embodiment, the first angle information may include a first angle representing an inclination of the incidence surface of the X-ray detector 520. In other words, the first angle information may include a first angle which is an angle between the incidence surface of the X-ray detector 520 and a horizontal surface. The second angle information may include a second angle representing an angle by which the X-ray radiator 510 has been rotated from a reference location in the predetermined direction. In other words, the second angle information may include a second angle representing an angle by which the X-ray radiator 510 is rotated clockwise from a position where the X-ray radiator 510 perpendicularly faces the horizontal surface. Accordingly, the driving controller 530 may determine the rotation angle for aligning the X-ray radiator 510 with the X-ray detector 520, based on a difference between the first angle and the second angle.

The driving controller 530 may determine the rotation direction for aligning the X-ray radiator 510 with the X-ray detector 520, based on the second angle information. For example, when the second angle information represents that the X-ray radiator 510 has been rotated clockwise by a predetermined angle, the driving controller 530 may determine the clockwise direction as the rotation direction.

According to an exemplary embodiment, since the X-ray detector 520 may include a sensor unit (not shown), the X-ray detector 520 may acquire the first angle information via the sensor unit. For example, the sensor unit may be a gyroscope sensor, a geomagnetic sensor, an inertial measurement unit (IMU), an accelerometer, a magnetometer, or a global positioning system (GPS) sensor. In detail, the X-ray detector 520 may measure a Pitch angle and a Roll angle of the X-ray detector 520 by using an acceleration sensor, and may acquire the measured Pitch angle and the measured Roll angle as the first angle information. The X-ray detector 520 may acquire a larger angle from among the measured Pitch angle and the measured Roll angle as the first angle.

The driving controller 530 may acquire the first angle information from the X-ray detector 520. According to an exemplary embodiment, the X-ray detector 520 may transmit the first angle information to a workstation (not shown) via a Transfer Control Protocol/Internet Protocol (TCP/IP). Then, the workstation may transmit the first service information to the driving controller 530 via the TCP/IP. The driving controller 530 may also acquire the second angle information from the X-ray detector 520. For example, the driving controller 530 may acquire the second angle information via a position sensor of the X-ray detector 520.

The driving controller 530 may transmit information about the determined rotation angle and information about the determined rotation direction to the driver 540. According to an exemplary embodiment, the driving controller 530 may transmit the information about the determined rotation angle and the information about the determined rotation direction to the driver 540 via a Controller Area Network (CAN).

The driver 540 may rotate the X-ray radiator 510 by the rotation angle determined by the driving controller 530, in the rotation direction determined by the driving controller 530. In other words, to align the X-ray radiator 510 with the X-ray detector 520, the driver 540 may rotate the X-ray radiator 510 according to the rotation angle and the rotation direction determined by the driving controller 530. According to an exemplary embodiment, the driver 540 may correspond to the first, second, and third motors 211, 212, and 213, the guide rail 220, the moving carriage 230, and the post frame 240 of FIG. 1.

Figure 5:
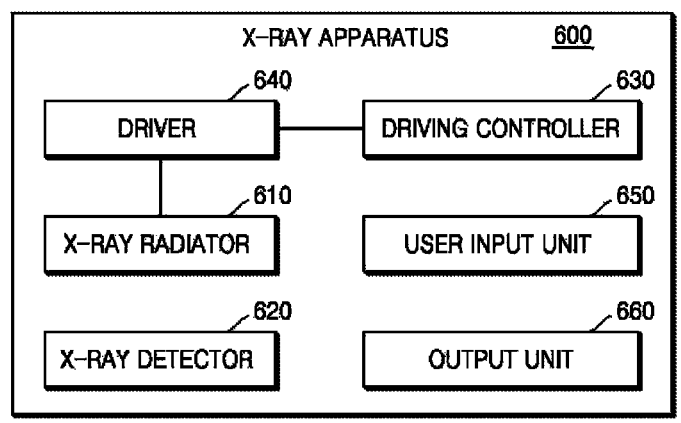
FIG. 5 is a block diagram of an X-ray apparatus according to an exemplary embodiment.

FIG. 5 is a block diagram of an X-ray apparatus 600 according to an exemplary embodiment.

The X-ray apparatus 600 may include an X-ray detector 620, an X-ray radiator 610, a driving controller 630, a driver 640, a user input unit 650, and an output unit 660. Only components related with the present exemplary embodiment from among the components of the X-ray apparatus 600 are shown in FIG. 5. It will be understood by one of ordinary skill in the art that general-use components other than the components illustrated in FIG. 5 may be further included.

The X-ray radiator 610, the X-ray detector 620, the driving controller 630, and the driver 640 may include the features of the X-ray radiator 510, the X-ray detector 520, the driving controller 530, and the driver 540 of FIG. 4, and thus redundant descriptions thereof will be omitted here.

The output unit 660 may display the first angle information and the second angle information on a screen thereof. According to an exemplary embodiment, the output unit 660 may display, on the screen thereof, a first angle representing an inclination of an incidence surface of the X-ray detector 620 with respect to a horizontal surface, and display, on the screen thereof, a second angle representing an angle by which the X-ray radiator 610 has been rotated from a direction in which the X-ray radiator 610 faces the horizontal surface. When the driver 640 rotates the X-ray radiator 610 by a rotation angle determined by the driving controller 630, the output unit 660 may display, on the screen thereof, information representing that the X-ray radiator 610 is aligned with the X-ray detector 620. According to another exemplary embodiment, when the driver 640 rotates the X-ray radiator 610 by the rotation angle determined by the driving controller 630, the output unit 660 may output a predetermined sound or a predetermined indicator such that a user or an object may recognize the fact that the X-ray radiator 610 is aligned with the X-ray detector 620.

The user input unit 650 may receive a command for controlling the X-ray apparatus 600, from the user. The user input unit 650 may receive a command regarding alignment between the X-ray radiator 610 and the X-ray detector 620 from the user. For example, the user input unit 650 may include a button commanding alignment between the X-ray radiator 610 and the X-ray detector 620. Accordingly, when the driver 640 receives the command regarding the alignment from the user via the user input unit 650, the driver 640 may rotate the X-ray radiator 610 according to the rotation angle and rotation direction determined by the driving controller 630. According to an exemplary embodiment, the output unit 660 and the user input unit 650 may provide the user with a user interface (UI) for manipulating the X-ray apparatus 600. The output unit 660 may display the UI.

The user input unit 650 may be a touch pad. In detail, the user input unit 650 may include a touch pad (not shown)

coupled with a display panel (not shown) included in the output unit 660. The output unit 660 displays a UI image on the display panel. When a user inputs a command by touching a certain point on the UI screen image, the touch pad may sense the input operation and recognize the command input by the user.

In detail, when the user input unit 650 is a touch pad and the user touches a certain point on the UI image, the user input unit 650 senses the touched point. Then, the user input unit 650 may transmit sensed information to the driving controller 630. Thereafter, the driving controller 630 may recognize a user's request or command corresponding to the sensed information and may perform the recognized user's request or command.

Figure 6A:
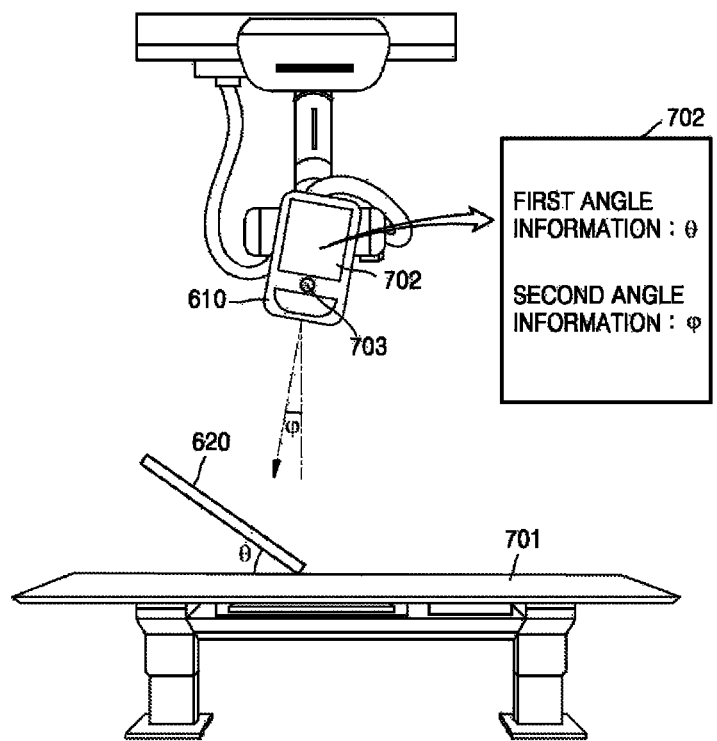
FIGS. 6A and 6B illustrate an exemplary embodiment of an X-ray apparatus which aligns an X-ray radiator with an X-ray detector.
Figure 6B:
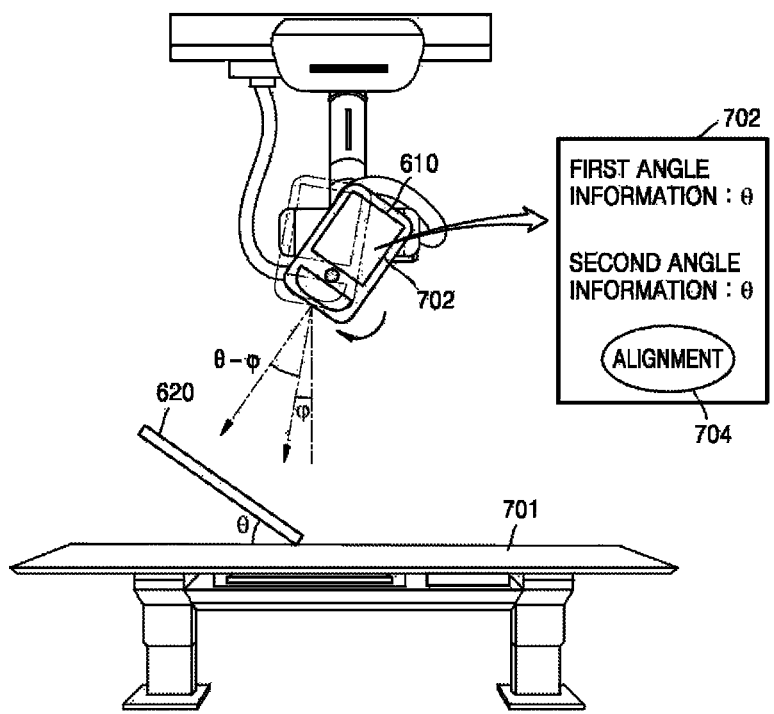

FIGS. 6A and 6B illustrate an exemplary embodiment of the X-ray apparatus 600 which aligns the X-ray radiator 610 with the X-ray detector 620.

Although not shown in FIGS. 6A and 6B, the X-ray apparatus 600 may further include other components that may be included in the X-ray apparatus 600, in addition to the X-ray radiator 610 and the X-ray detector 620.

First, in FIG. 6A, the X-ray detector 620 may be inclined while maintaining a predetermined angle θ with respect to a table 701. In other words, a user may tilt the X-ray detector 620 on the table 701 at the predetermined angle θ. The X-ray radiator 610 may rotate clockwise by an angle φ from a position where the X-ray radiator 610 perpendicularly faces the table 701. In other words, the user may rotate the X-ray radiator 610 by the angle φ from a position of the X-ray radiator 610 when perpendicularly viewing the table 701.

The driving controller 630 may acquire the angle θ at which the X-ray detector 620 is tilt, as the first angle information, and may acquire the angle φ by which the X-ray radiator 610 has been rotated, as the second angle information. The driving controller 630 may also acquire, as the second angle information, the fact that a direction in which the X-ray radiator 610 has been rotated by the angle φ is clockwise.

The output unit 660 may display the angle θ as the first angle information and the angle φ as the second angle information, on a screen 702.

The user input unit 650 may receive a command regarding alignment between the X-ray radiator 610 and the X-ray detector 620 from the user via a button 703.

The driving controller 630 may determine a rotation angle θ-φ for aligning the X-ray radiator 610 with the X-ray detector 620, based on the angle θ as the acquired first angle information and the angle φ as the acquired second angle information. The driving controller 630 may determine the rotation direction for aligning the X-ray radiator 610 with the X-ray detector 620, to be clockwise, based on the acquired second angle information. The driving controller 630 may transmit the determined rotation angle θ-φ and information representing that the rotation direction is clockwise, to the driver 640.

As shown in FIG. 6B, the driver 640 may rotate the X-ray radiator 610 clockwise at the rotation angle θ-φ, based on information received from the driving controller 630. In other words, the driver 640 may rotate the X-ray radiator 610 clockwise at the rotation angle θ-φ in order to align the X-ray radiator 610 with the X-ray detector 620.

Then, the output unit 660 may display the angle θ by which the X-ray radiator 610 has been rotated clockwise, on the screen 702. The output unit 660 may also display information 704 representing that the X-ray radiator 610 is aligned with the X-ray detector 620, on the screen 702.

Figure 7:
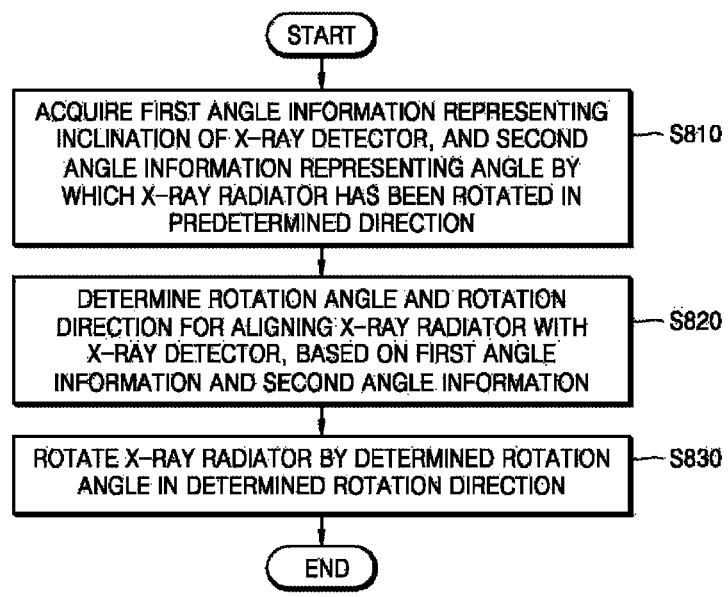
FIG. 7 is a flowchart of a method of operating an X-ray apparatus, according to an exemplary embodiment.

FIG. 7 is a flowchart of a method of operating the X-ray apparatuses 500 and 600, according to an exemplary embodiment.

The method of FIG. 7 may be performed by the X-ray apparatuses 500 and 600 of FIGS. 4 and 5, and a redundant description thereof will be omitted here.

In operation S810, the X-ray apparatuses 500 and 600 may acquire first angle information representing an inclination of an X-ray detector, and second angle information representing an angle by which an X-ray radiator has been rotated in a predetermined direction. According to an exemplary embodiment, the first angle information may include a first angle representing the inclination of an incidence surface of the X-ray detector. In other words, the first angle information may include a first angle which is an angle between the incidence surface of the X-ray detector and a horizontal surface. The second angle information may include a second angle representing an angle by which the X-ray radiator has been rotated from a reference location in the predetermined direction. In other words, the second angle information may include a second angle representing an angle by which the X-ray radiator has been rotated clockwise from a position where the X-ray radiator perpendicularly faces the horizontal surface.

The X-ray apparatuses 500 and 600 may display the first angle information and the second angle information on screens thereof. According to an exemplary embodiment, the X-ray apparatuses 500 and 600 may display, on the screens thereof, the first angle representing an inclination of the incidence surface of the X-ray detector with respect to the horizontal surface, and display, on the screens thereof, the second angle representing the angle by which the X-ray radiator has been rotated from a direction in which the X-ray radiator faces the horizontal surface.

In operation S820, the X-ray apparatuses 500 and 600 may determine a rotation angle and rotation direction for aligning the X-ray radiator with the X-ray detector, based on the first angle information and the second angle information. In more detail, the X-ray apparatuses 500 and 600 may determine the rotation angle for aligning the X-ray radiator with the X-ray detector, based on a difference between the first angle and the second angle.

The X-ray apparatuses 500 and 600 may determine the rotation direction for aligning the X-ray radiator with the X-ray detector, based on the second angle information. For example, when the second angle information represents that the X-ray radiator has been rotated clockwise by a predetermined angle, the X-ray apparatuses 500 and 600 may determine the clockwise direction as the rotation direction.

In operation S830, the X-ray apparatuses 500 and 600 may rotate the X-ray radiator by the determined rotation angle in the determined rotation direction. In other words, to align the X-ray radiator with the X-ray detector, the X-ray apparatuses 500 and 600 may rotate the X-ray radiator according to the determined rotation angle and the determined rotation direction.

When the X-ray radiator has been rotated by the determined rotation angle in the determined rotation direction, the X-ray apparatuses 500 and 600 may display information representing that the X-ray radiator is aligned with the X-ray detector, on the screens thereof. According to another exemplary embodiment, when the X-ray radiator has been rotated by the determined rotation angle in the determined rotation direction, the X-ray apparatuses 500 and 600 may output a predetermined sound or a predetermined indicator such that a user or an object may be aware of the fact that the X-ray radiator is aligned with the X-ray detector.

The X-ray apparatuses 500 and 600 may receive a command for controlling the X-ray apparatuses 500 and 600, from the user. The X-ray apparatuses 500 and 600 may also receive a command regarding alignment between the X-ray radiator and the X-ray detector, from the user. Accordingly, in response to the user command regarding the alignment between the X-ray radiator and the X-ray detector, the X-ray apparatuses 500 and 600 may rotate the X-ray radiator according to the determined rotation angle and the determined rotation direction. According to an exemplary embodiment, the X-ray apparatuses 500 and 600 may provide the user with a UI for manipulating the X-ray apparatuses 500 and 600.

Figure 8:
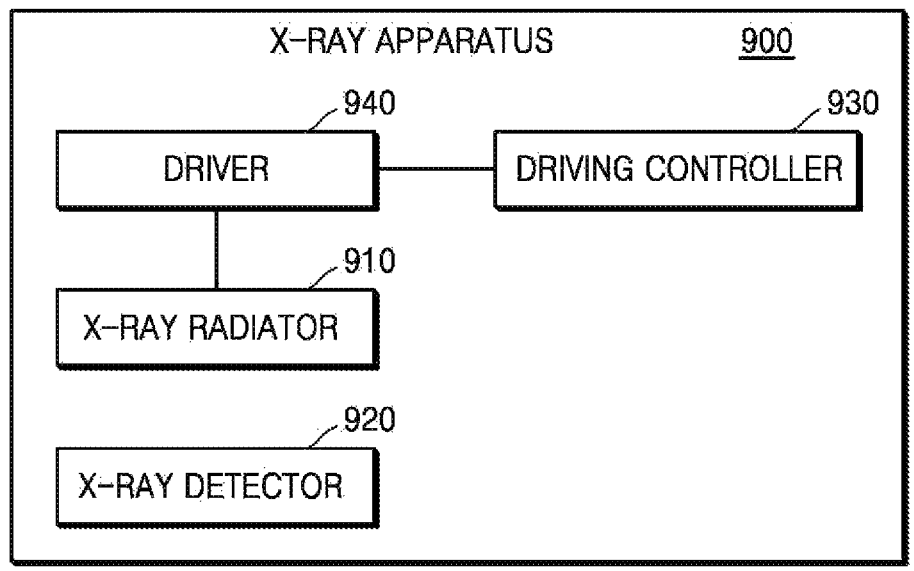
FIG. 8 is a block diagram of an X-ray apparatus according to an exemplary embodiment.

FIG. 8 is a block diagram of an X-ray apparatus 900 according to an exemplary embodiment.

The X-ray apparatus 900 may include an X-ray detector 920, an X-ray radiator 910, a driving controller 930, and a driver 940. Only components related with the present exemplary embodiment from among the components of the X-ray apparatus 900 are shown in FIG. 8. It will be understood by one of ordinary skill in the art that general-use components other than the components illustrated in FIG. 8 may be further included.

Since the X-ray radiator 910 may include the features of the X-ray radiator 120 of FIGS. 1-3, a redundant description thereof will be omitted here. Since the X-ray detector 920 may include the features of the X-ray detector 130 of FIGS. 1-3, a redundant description thereof will be omitted here.

The driving controller 930 may acquire motion information representing that the X-ray detector 920 is rotated in a predetermined direction by a predetermined angle, and may determine a rotation angle and rotation direction for aligning the X-ray radiator 910 with the X-ray detector 920, based on the acquired motion information. In other words, the driving controller 930 may determine the predetermined angle by which the X-ray detector 920 has been rotated in the predetermined direction, as the rotation angle, based on the motion information. The driving controller 930 may determine the predetermined direction in which the X-ray detector 920 has been rotated, based on the motion information. For example, when the motion information represents that the X-ray detector 920 has been rotated clockwise by 30 degrees, the driving controller 930 may determine the rotation angle to be 30 degrees, and determine the rotation direction to be clockwise.

The motion information may represent that the X-ray detector 920 has been rotated by the predetermined angle in the predetermined direction with respect to one edge of the incidence surface of the X-ray detector 920. The predetermined direction may be clockwise or counterclockwise. Since the X-ray detector 920 may include a sensor unit (not shown), the X-ray detector 920 may acquire the motion information via the sensor unit. For example, the sensor unit may be a gyroscope sensor, a geomagnetic sensor, an inertial measurement unit (IMU), an accelerometer, a magnetometer, or a global positioning system (GPS) sensor. The motion information of the X-ray detector 920 may represent a moving angle of the X-ray detector 920 that is detected by the sensor unit during a predetermined time interval. For example, the predetermined time interval may include a time interval such as one second, ten seconds, or one minute. Since the motion information of the X-ray detector 920 may be sensed using any of various methods that are widely used in the art, a method of sensing the motion information of the X-ray detector 920 is not limited to a specific method.

The driving controller 930 may acquire the motion information from the X-ray detector 920. According to an exemplary embodiment, the X-ray detector 920 may transmit the motion information to a workstation (not shown) via a TCP/IP. Then, the workstation may transmit the motion information to the driving controller 930 via the TCP/IP.

The driving controller 930 may transmit information about the determined rotation angle and information about the determined rotation direction to the driver 940. According to an exemplary embodiment, the driving controller 930 may transmit the information about the determined rotation angle and the information about the determined rotation direction to the driver 940 via a CAN.

The driver 940 may rotate the X-ray radiator 910 according to the rotation angle and rotation direction determined by the driving controller 930. In other words, to align the X-ray radiator 910 with the X-ray detector 920, the driver 940 may rotate the X-ray radiator 910 according to the rotation angle and rotation direction determined by the driving controller 930. According to an exemplary embodiment, the driver 940 may correspond to the first, second, and third motors 211, 212, and 213, the guide rail 220, the moving carriage 230, and the post frame 240 of FIG. 2.

Figure 9:
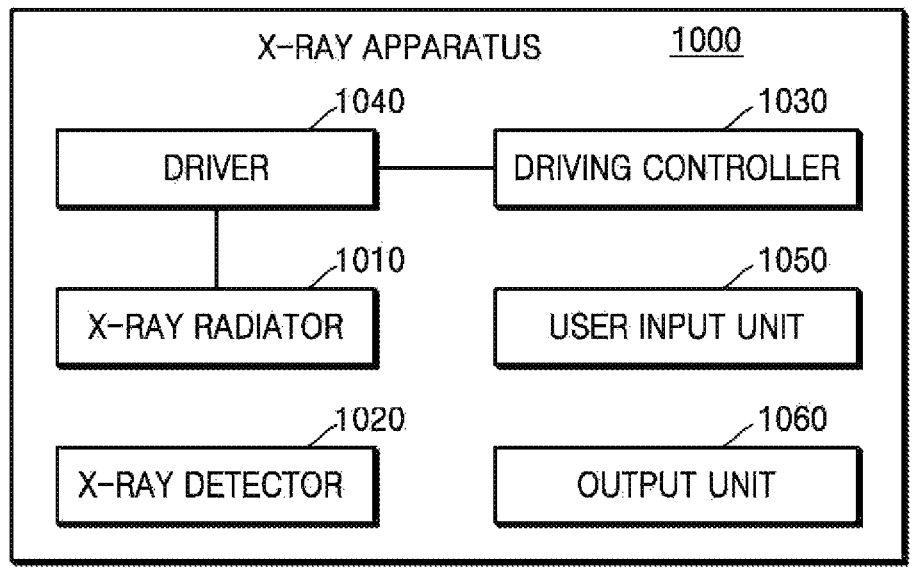
FIG. 9 is a block diagram of an X-ray apparatus according to an exemplary embodiment.

FIG. 9 is a block diagram of an X-ray apparatus 1000 according to an exemplary embodiment.

An X-ray radiator 1010, an X-ray detector 1020, a driving controller 1030, and a driver 1040 may include the features of the X-ray radiator 910, the X-ray detector 920, the driving controller 930, and the driver 940 of FIG. 8, and thus redundant descriptions thereof will be omitted here.

The user input unit 1050 may receive a command for controlling the X-ray apparatus 1000, from the user. The user input unit 1050 may receive a command regarding alignment between the X-ray radiator 1010 and the X-ray detector 1020 from the user. For example, the user input unit 1050 may include a button commanding alignment between the X-ray radiator 1010 and the X-ray detector 1020. Accordingly, when the driver 1040 receives the command regarding the alignment from the user via the user input unit 1050, the driver 1040 may rotate the X-ray radiator 1010 according to the rotation angle and rotation direction determined by the driving controller 1030. According to an exemplary embodiment, the output unit 1060 and the user input unit 1050 may provide the user with a UI for manipulating the X-ray apparatus 1000.

When the driver 1040 rotates the X-ray radiator 1010 by the rotation angle determined by the driving controller 1030, the output unit 1060 may display, on a screen thereof, information representing that the X-ray radiator 1010 is aligned with the X-ray detector 1020. According to another exemplary embodiment, when the driver 1040 rotates the X-ray radiator 1010 by the rotation angle determined by the driving controller 1030, the output unit 1060 may output a predetermined sound or a predetermined indicator such that a user or an object may be aware of the fact that the X-ray radiator 1010 is aligned with the X-ray detector 1020.

Figure 10A:
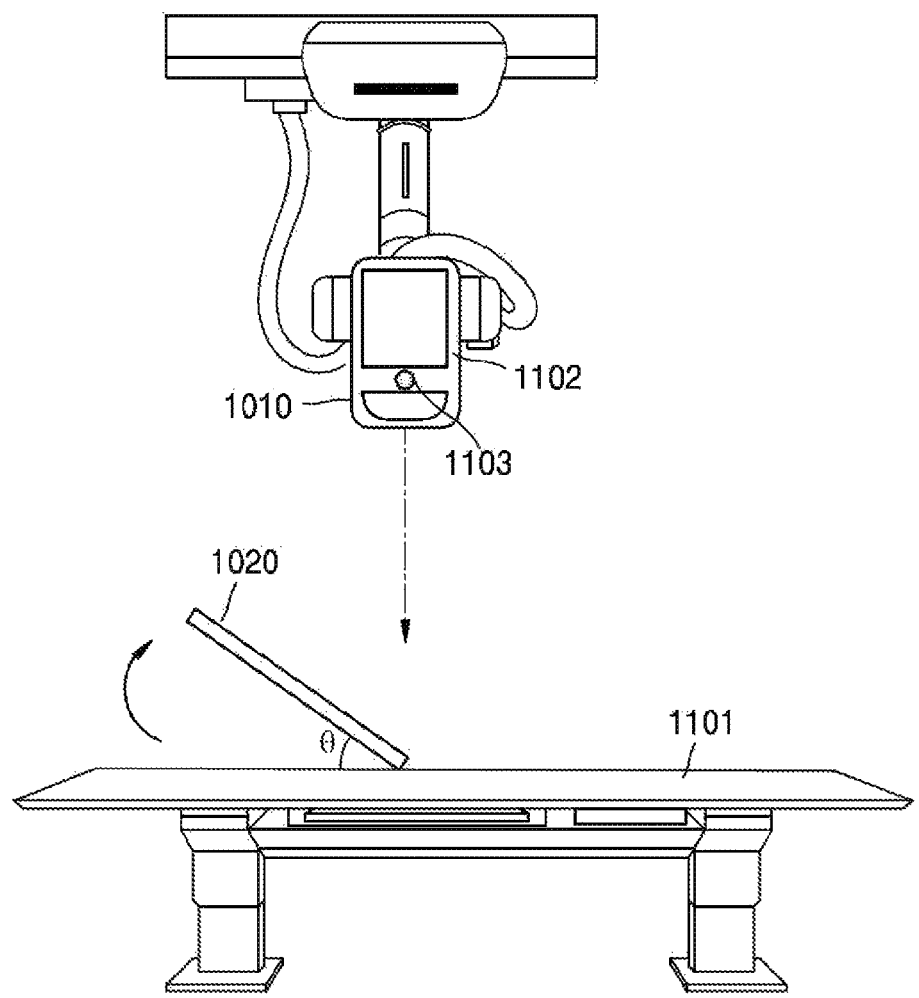
FIGS. 10A and 10B illustrate an exemplary embodiment of an X-ray apparatus which aligns an X-ray radiator with an X-ray detector.
Figure 10B:
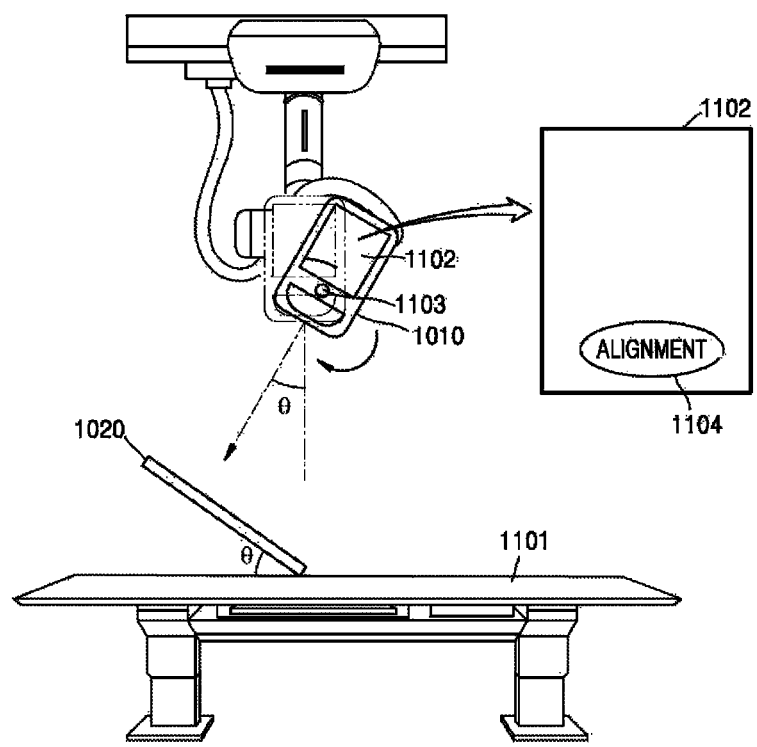

FIGS. 10A and 10B illustrate an exemplary embodiment of the X-ray apparatus 1000 which aligns the X-ray radiator 1010 with the X-ray detector 1020.

Although not shown in FIGS. 10A and 10B, the X-ray apparatus 1000 may further include other components that may be included in the X-ray apparatus 1000, in addition to the X-ray radiator 1010 and the X-ray detector 1020.

First, in FIG. 10A, the X-ray detector 1020 may be rotated by a predetermined angle θ clockwise with respect to one edge of an incidence surface of the X-ray detector 1020 relative to a horizontal surface 1101. In other words, a user may rotate the X-ray detector 1020 by the angle θ clockwise with respect to one edge of the incidence surface of the X-ray detector 1020 relative to a horizontal surface 1101.

The driving controller 1030 may acquire motion information representing that the X-ray detector 1020 has been rotated clockwise by the angle θ.

The user input unit 1050 may receive a command regarding alignment between the X-ray radiator 1010 and the X-ray detector 1020 from the user via a button 1103.

The driving controller 1030 may determine a rotation angle θ for aligning the X-ray radiator 1010 with the X-ray detector 1020, and determine a rotation direction to be clockwise, based on the acquired motion information. The driving controller 1030 may transmit the determined rotation angle θ and information about the clockwise direction, to the driver 1040.

As shown in FIG. 10B, the driver 1040 may rotate the X-ray radiator 1010 clockwise by the rotation angle θ, based on information received from the driving controller 1030. In other words, the driver 1040 may rotate the X-ray radiator 1010 clockwise by the rotation angle θ in order to align the X-ray radiator 1010 with the X-ray detector 1020.

Then, the output unit 1060 may display information 1104 representing that the X-ray radiator 1010 is aligned with the X-ray detector 1020, on a screen 1102.

Figure 11:
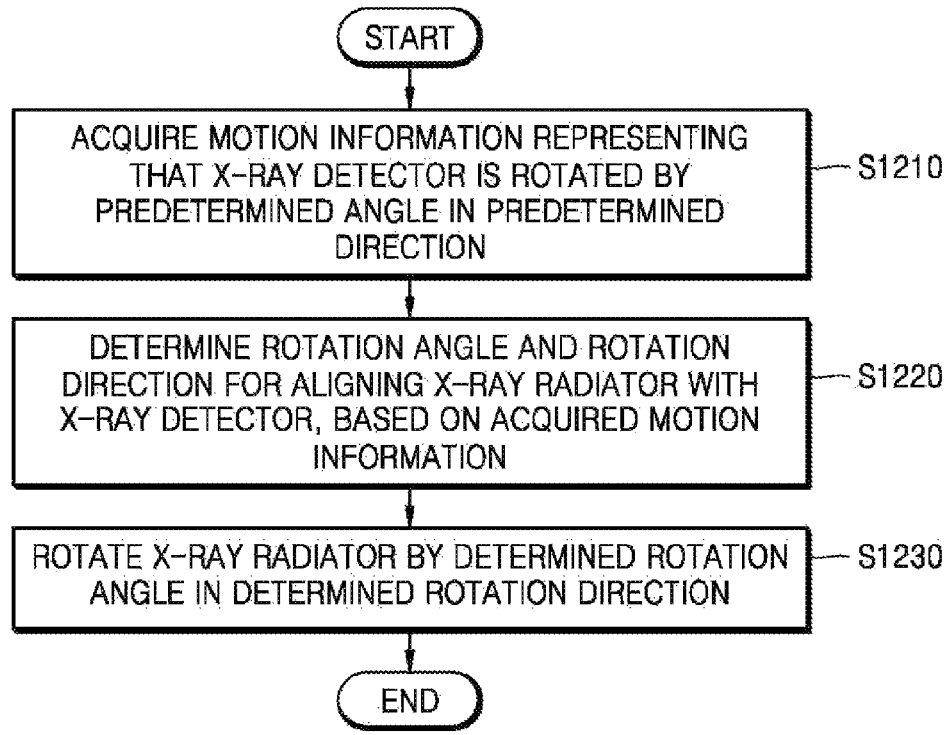
FIG. 11 is a flowchart of a method of operating an X-ray apparatus, according to an exemplary embodiment.

FIG. 11 is a flowchart of a method of operating the X-ray apparatuses 900 and 1000, according to an exemplary embodiment.

The method of FIG. 11 may be performed by the X-ray apparatuses 900 and 1000 of FIGS. 8 and 9, and a redundant description thereof will be omitted here.

In operation S1210, the X-ray apparatuses 900 and 1000 may acquire motion information representing that an X-ray detector is rotated by a predetermined angle in a predetermined direction. The motion information may represent that the X-ray detector has been rotated by the predetermined angle in the predetermined direction with respect to one edge of an incidence surface of the X-ray detector. The predetermined direction may be clockwise or counterclockwise.

In operation S1220, the X-ray apparatuses 900 and 1000 may determine a rotation angle and rotation direction for aligning an X-ray radiator with the X-ray detector, based on the acquired motion information. In other words, the X-ray apparatuses 900 and 1000 may determine the predetermined angle by which the X-ray detector has been rotated in the predetermined direction, as the rotation angle, based on the motion information. The X-ray apparatuses 900 and 1000 may determine the predetermined direction in which the X-ray detector has been rotated, based on the motion information. For example, when the motion information represents that the X-ray detector has been rotated clockwise by 30 degrees, the X-ray apparatuses 900 and 1000 may determine the rotation angle to be 30 degrees, and determine the rotation direction to be clockwise.

In operation S1230, the X-ray apparatuses 900 and 1000 may rotate the X-ray radiator by the determined rotation angle in the determined rotation direction. In other words, to align the X-ray radiator with the X-ray detector, the X-ray apparatuses 900 and 1000 may rotate the X-ray radiator according to the determined rotation angle and the determined rotation direction.

When the X-ray radiator has been rotated at the determined rotation angle in the determined rotation direction, the X-ray apparatuses 900 and 1000 may display information representing that the X-ray radiator is aligned with the X-ray detector, on screens of the X-ray apparatuses 900 and 1000. According to another exemplary embodiment, when the X-ray radiator has been rotated by the determined rotation angle in the determined rotation direction, the X-ray apparatuses 900 and 1000 may output a predetermined sound or a predetermined indicator such that a user or an object may be aware of the fact that the X-ray radiator is aligned with the X-ray detector.

The X-ray apparatuses 900 and 1000 may receive a command for controlling the X-ray apparatuses 900 and 1000, from the user. The X-ray apparatuses 900 and 1000 may also receive a command regarding alignment between the X-ray radiator and the X-ray detector, from the user. Accordingly, in response to the user command regarding the alignment between the X-ray radiator and the X-ray detector, the X-ray apparatuses 900 and 1000 may rotate the X-ray radiator according to the determined rotation angle and the determined rotation direction. According to an exemplary embodiment, the X-ray apparatuses 900 and 1000 may provide the user with a UI for manipulating the X-ray apparatuses 900 and 1000.

Figure 12:
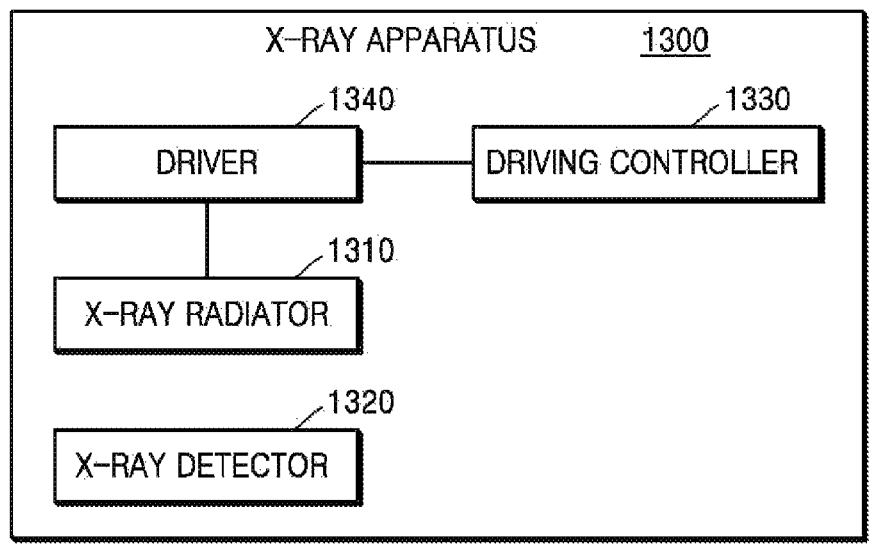
FIG. 12 is a block diagram of an X-ray apparatus according to an exemplary embodiment.

FIG. 12 is a block diagram of an X-ray apparatus 1300 according to an exemplary embodiment.

The X-ray apparatus 1300 may include an X-ray detector 1320, an X-ray radiator 1310, a driving controller 1330, and a driver 1340. Only components related with the present exemplary embodiment from among the components of the X-ray apparatus 1300 are shown in FIG. 12. It will be understood by one of ordinary skill in the art that general-use components other than the components illustrated in FIG. 12 may be further included.

Since the X-ray radiator 1310 may include the features of the X-ray radiator 120 of FIGS. 1-3, a redundant description thereof will be omitted here. Since the X-ray detector 1320 may include the features of the X-ray detector 130 of FIGS. 1-3, a redundant description thereof will be omitted here.

The driving controller 1330 may acquire angle information representing an inclination of the X-ray detector 1320, information about a preset point on the X-ray detector 1320, and information about a Source to Image-receptor Distance (SID) which is a distance between the preset point and the X-ray radiator 1310, and may determine a location and a rotation angle for aligning the X-ray radiator 1310 with the X-ray detector 1320 while maintaining the SID, based on the acquired pieces of information. The SID described herein may be described as a distance between the X-ray detector 1320 and the X-ray radiator 1310. In more detail, the SID described herein may be described as a distance between the X-ray detector 1320 and an X-ray source (not shown) of the X-ray radiator 1310.

The angle information representing the inclination of the X-ray detector 1320 may include an angle representing an inclination of an incidence surface of the X-ray detector 1320. In other words, the angle information may include an angle between the incidence surface of the X-ray detector 1320 and a horizontal surface.

According to an exemplary embodiment, since the X-ray detector 1320 may include a sensor unit (not shown), the X-ray detector 1320 may acquire the angle information via the sensor unit. For example, the sensor unit may be a gyroscope sensor, a geomagnetic sensor, an inertial measurement unit (IMU), an accelerometer, a magnetometer, or a global positioning system (GPS) sensor. In detail, the X-ray detector 1320 may measure a Pitch angle and a Roll angle of the X-ray detector 1320 by using an acceleration sensor, and may acquire the measured Pitch angle and the measured Roll angle as the angle information. The X-ray detector 1320 may acquire a larger angle from among the measured Pitch angle and the measured Roll angle as the angle information.

According to an exemplary embodiment, the driving controller 1330 may acquire the angle information from the X-ray detector 1320. According to an exemplary embodiment, the X-ray detector 1320 may transmit the angle information to a workstation (not shown) via a TCP/IP. Then, the workstation may transmit the angle information to the driving controller 1330 via the TCP/IP.

According to an exemplary embodiment, the driving controller 1330 may acquire the information about the preset point on the X-ray detector 1320, based on a point on the X-ray detector 1320 that is viewed by the X-ray radiator 1310. In more detail, when the X-ray radiator 1310 radiates light on the X-ray detector 1320 via a radiation window including cross wires, the driving controller 1330 may set an intersection between the cross wires formed on the X-ray detector 1320 to be the preset point. Accordingly, a user may manipulate a direction of the X-ray radiator 1310 so that the X-ray radiator 1310 faces a point on the X-ray detector 1320 desired by the user, and the driving controller 1330 may set the point on the X-ray detector 1320 desired by the user to be the preset point on the X-ray detector 1320.

According to an exemplary embodiment, the driving controller 1330 may acquire information about an SID which is a distance between the preset point on the X-ray detector 1320 and the X-ray radiator 1310, based on a user input. According to another exemplary embodiment, the driving controller 1330 may calculate the distance between the X-ray radiator 1310 and the preset point on the X-ray detector 1320 and acquire the calculated distance as information about the SID. For example, the driving controller 1330 may acquire the information about the SID, based on an image acquired by an image acquirer (not shown). As another example, the driving controller 1330 may acquire the information about the SID, by using a device which generates energy such as ultrasound waves, infrared, or radio frequency (RF) and a device which receives energy reflected by the X-ray detector 1320.

The driving controller 1330 may determine the location and rotation angle for aligning the X-ray radiator 1310 with the X-ray detector 1320 while maintaining the SID, based on the acquired pieces of information. In more detail, the driving controller 1330 may determine a rotation angle for aligning the X-ray radiator 1310 with the X-ray detector 1320, based on the angle information of the X-ray detector 1320, and may determine a location at which the X-ray radiator 1310 is to be positioned to maintain the SID from the X-ray detector 1320, based on the information about the preset point on the X-ray detector 1320 and the information about the SID. For example, in a Global Coordinate that is expressed as an Inertial Frame in which a location within an X-ray scan space is the origin, the driving controller 1330 may calculate a position vector of the X-ray radiator 1310 and a position vector of the preset point on the X-ray detector 1320 and may determine the location at which the X-ray radiator 1310 is to be positioned to maintain the SID from the X-ray detector 1320, based on the calculated position vectors and the SID. In this case, since a position vector of an object within an X-ray scan space may be acquired using any of various sensors or apparatuses according to various methods, such as methods of using light, electromagnetic waves, sound waves, a magnetic field, and an electric field, a method of acquiring the position vector of the X-ray radiator 1310 or the position vector of the preset point on the X-ray detector 1320 is not limited to a specific method.

The driver 1340 may move and rotate the X-ray radiator 1310 according to the location and the rotation angle determined by the driving controller 1330. In other words, the driver 1340 may move and rotate the X-ray radiator 1310 in order to align the X-ray radiator 1310 with the X-ray detector 1320 while maintaining the SID therebetween.

According to another exemplary embodiment, the driving controller 1330 may acquire angle information representing an inclination of the X-ray detector 1320, information about a preset point on an object located between the X-ray radiator 1310 and the X-ray detector 1320, and information about a Source to Object Distance (SOD) which is a distance between the preset point on the object and the X-ray radiator 1310, and may determine a location and a rotation angle for aligning the X-ray radiator 1310 with the X-ray detector 1320 while maintaining the SOD, based on the acquired pieces of information. The SOD described herein may be described as a distance between the object and the X-ray radiator 1310. In more detail, the SOD described herein may be described as a distance between the object and an X-ray source (not shown) of the X-ray radiator 1310.

According to an exemplary embodiment, the driving controller 1330 may acquire the information about the preset point on the object, based on a point on the object that is viewed by the X-ray radiator 1310. For example, a user may manipulate a direction of the X-ray radiator 1310 so that the X-ray radiator 1310 faces a point on the object desired by the user, and the driving controller 1330 may acquire information about the preset point on the object based on the point on the object desired by the user. In more detail, when the X-ray radiator 1310 radiates light on the object via a radiation window including cross wires, the driving controller 1330 may set an intersection between the cross wires formed on the object to be the preset point.

Figure 19:
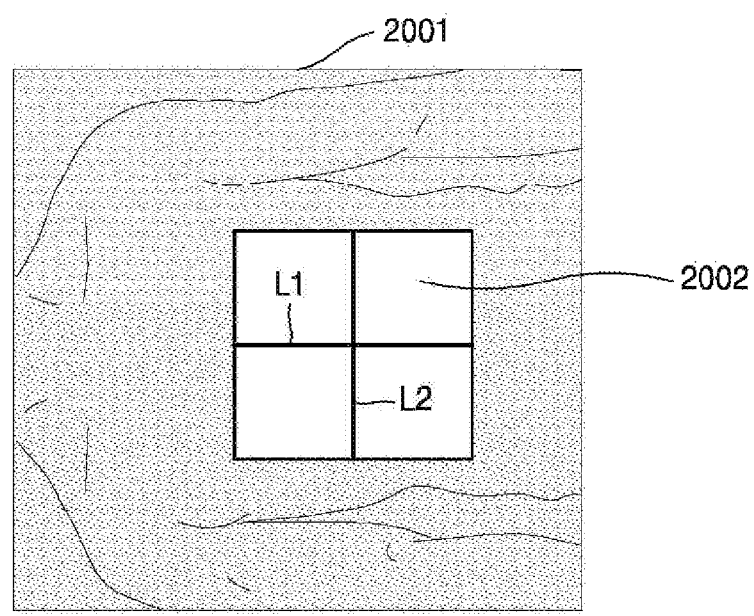
Figure 20:
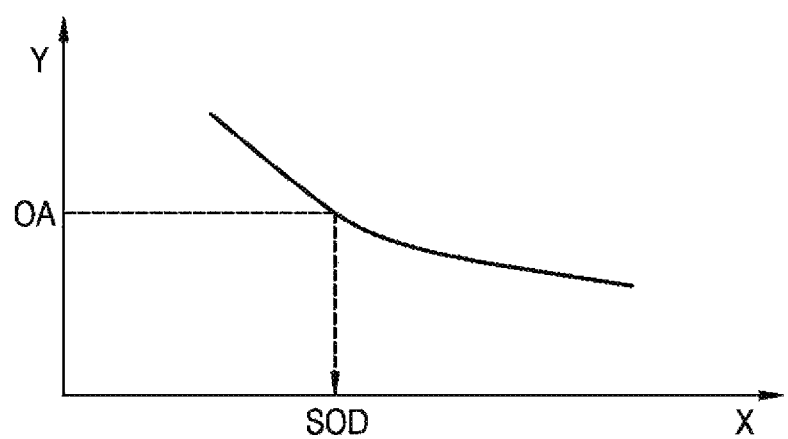

According to an exemplary embodiment, the driving controller 1330 may acquire the information about the SOD which is a distance between the preset point on the object and the X-ray radiator 1310, based on a user input. According to another exemplary embodiment, the driving controller 1330 may calculate the distance between the X-ray radiator 1310 and the preset point on the object and acquire the calculated distance as information about the SOD. For example, as shown in FIGS. 19-20, the driving controller 1330 may acquire the information about the SOD, based on an image acquired by an image acquirer (not shown). As another example, the driving controller 1330 may acquire the information about the SOD, by using a device which generates energy, such as ultrasound waves, infrared, or RF, and a device which receives energy reflected by the X-ray detector 1320.

The driving controller 1330 may determine the location and rotation angle for aligning the X-ray radiator 1310 with the X-ray detector 1320 while maintaining the SOD, based on the acquired pieces of information. In more detail, the driving controller 1330 may determine a rotation angle for aligning the X-ray radiator 1310 with the X-ray detector 1320, based on the angle information of the X-ray detector 1320, and may determine a location at which the X-ray radiator 1310 is to be positioned to maintain the SOD from the X-ray detector 1320, based on the information about the preset point on the X-ray detector 1320 and the information about the SOD.

The driver 1340 may move and rotate the X-ray radiator 1310 according to the location and the rotation angle determined by the driving controller 1330. In other words, the driver 1340 may move and rotate the X-ray radiator 1310 in order to align the X-ray radiator 1310 with the X-ray detector 1320 while maintaining the SOD therebetween.

Figure 13:
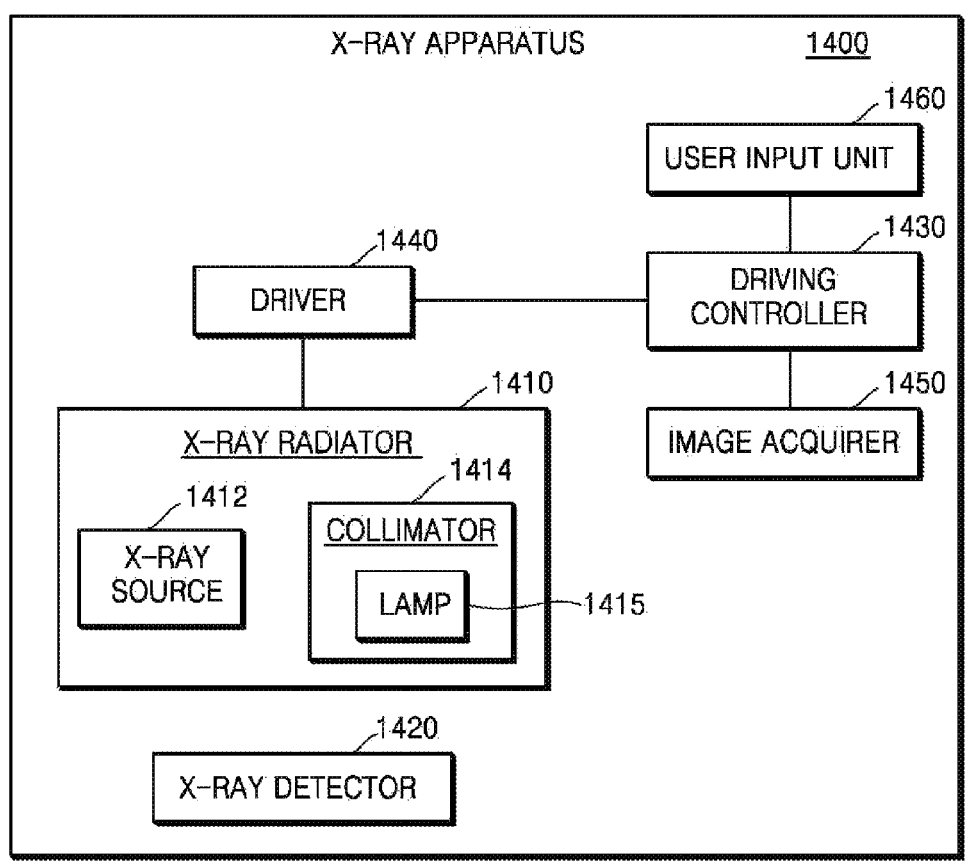
FIG. 13 is a block diagram of an X-ray apparatus according to an exemplary embodiment.

FIG. 13 is a block diagram of an X-ray apparatus 1400 according to an exemplary embodiment.

The X-ray apparatus 1400 may include an X-ray detector 1420, an X-ray radiator 1410, a driving controller 1430, a driver 1440, an image acquirer 1450, and a user input unit 1460. Only components related with the present exemplary embodiment from among the components of the X-ray apparatus 1400 are shown in FIG. 13. It will be understood by one of ordinary skill in the art that general-use components other than the components illustrated in FIG. 13 may be further included.

The X-ray radiator 1410, the X-ray detector 1420, the driving controller 1430, and the driver 1440 may include the features of the X-ray radiator 1310, the X-ray detector 1320, the driving controller 1330, and the driver 1340 of FIG. 12, and thus redundant descriptions thereof will be omitted here.

The X-ray radiator 1410 includes an X-ray source 1412 and a collimator 1414.

The X-ray source 1412 may radiate an X-ray. The collimator 1414 may adjust a radiation area of the X-ray that is radiated by the X-ray source 1412. The collimator 1414 includes a lamp 1415. The lamp 1415 may be turned on and off. The lamp 1415 may be implemented by using any of various illuminators. When the lamp 1415 is turned on, light is radiated by the lamp 1415.

Figure 14:
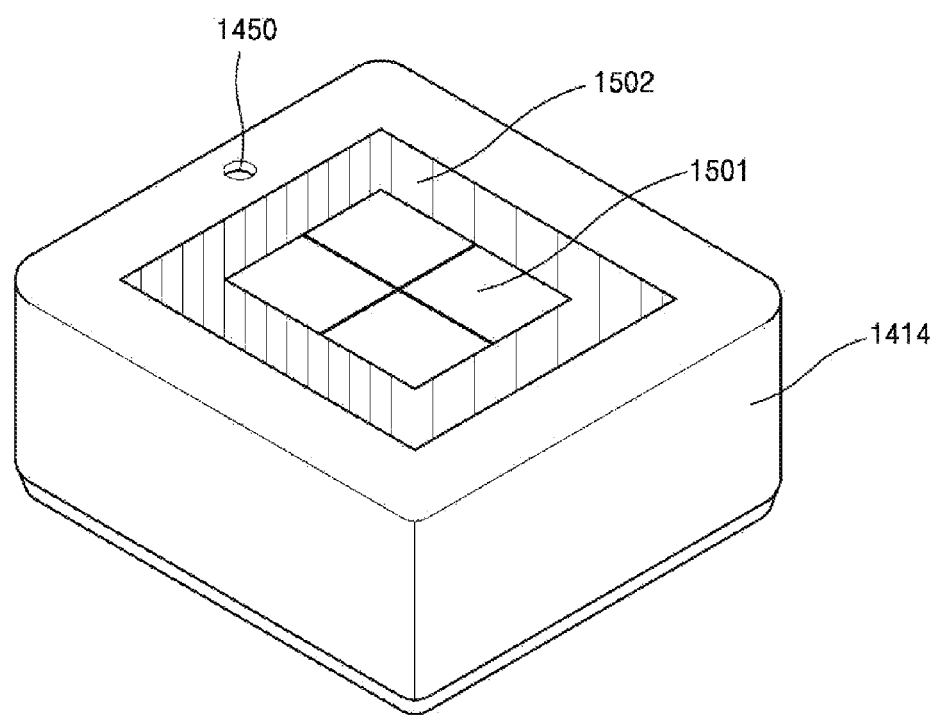
FIG. 14 illustrates an exemplary embodiment of a collimator included in the X-ray apparatus of FIG. 13.

FIG. 14 illustrates an exemplary embodiment of the collimator 1414 included in the X-ray apparatus 1400 of FIG. 13.

Referring to FIG. 14, the collimator 1414 may include a radiation window 1501 and a shutter 1502. Although not shown in FIG. 14, the collimator 1414 may include the lamp 1415 of FIG. 13.

The X-ray may be radiated by the X-ray source 1412 via the radiation window 1501 of the collimator 1414. When the lamp 1415 of the collimator 1414 is turned on, light may be radiated via the radiation window 1501 of the collimator 1414. In other words, the radiation window 1501 may transmit light from the lamp 1415 or the X-ray from the X-ray source 1412. In FIG. 14, the radiation window 1501 is rectangular, and includes cross lines. However, the rectangular radiation window 1501 of FIG. 14 is only an example, and the shape of the radiating window 1501 is not limited thereto.

The shutter 1502 may adjust the size of the radiation window 1501. The collimator 1414 may adjust a radiation area of X-ray by adjusting the size of the radiation window 1501 via the shutter 1502.

Since light from the lamp 1415 and the X-ray from the X-ray source 1412 are radiated via the radiation window 1501, a radiation area of light from the lamp 1415 may correspond to the radiation area of the X-ray. Accordingly, before the X-ray source 1412 radiates the X-ray, a user may check or adjust the radiation area of the X-ray by using the radiation area of light from the lamp 1415.

As shown in FIG. 14, the image acquirer 1450 may be attached to the collimator 1414. However, FIG. 14 is only an example, and a location of the image acquirer 1450 within the X-ray apparatus 1400 is not limited thereto.

The image acquirer 1450 of FIG. 13 may acquire a detector image by photographing the X-ray detector 1420 while the lamp 1415 is being turned on, and may acquire an object image by photographing an object put on the X-ray detector 1420. The image acquirer 1450 may be implemented by using various photographing apparatuses such as a camera and a camcorder.

The driving controller 1430 may acquire an SID which is a distance between the X-ray radiator 1410 and the X-ray detector 1420, based on the detector image acquired by the image acquirer 1450. In more detail, the driving controller 1430 may acquire information about a distance between a point on the X-ray detector 1420 corresponding to each pixel of the detector image and the X-ray radiator 1410, based on the detector image acquired by the image acquirer 1450. Accordingly, the driving controller 1430 may acquire an SID between a preset point on the X-ray detector 1430 and the X-ray radiator 1410, based on the detector image.

The driving controller 1430 may determine a location and a rotation angle for aligning the X-ray radiator 1410 with the X-ray detector 1420 while maintaining the SID, based on angle information representing an inclination of the X-ray detector 1420, information about the preset point on the X-ray detector 1420, and information about the SID between the preset point on the X-ray detector 1420 and the X-ray radiator 1410.

The user input unit 1460 may receive a command for controlling the X-ray apparatus 1400, from the user. The user input unit 1460 may receive a command regarding alignment between the X-ray radiator 1410 and the X-ray detector 1420 from the user. Accordingly, when the user input unit 1460 receives the command regarding the alignment from the user, the driving controller 1430 may determine the location and rotation angle for aligning the X-ray radiator 1410 with the X-ray detector 1420 while maintaining the SID. When the user input unit 1460 receives the command regarding the alignment from the user, the driver 1440 may move and rotate the X-ray radiator 1410 according to the location and rotation angle determined by the driving controller 1430.

According to another exemplary embodiment, the driving controller 1430 may acquire an SOD which is a distance between the object and the X-ray radiator 1410, based on the object image acquired by the image acquirer 1450. In more detail, the driving controller 1430 may acquire information about a distance between a point on the object corresponding to each pixel of the object image and the X-ray radiator 1410, based on the object image acquired by the image acquirer 1450. Accordingly, the driving controller 1430 may acquire an SOD between a preset point on the object and the X-ray radiator 1410, based on the object image. An exemplary embodiment in which the driving controller 1430 acquires the SOD will be described in detail later with reference to FIGS. 19-20.

The driving controller 1430 may determine a location and a rotation angle for aligning the X-ray radiator 1410 with the X-ray detector 1420 while maintaining the SOD, based on angle information representing an inclination of the X-ray detector 1420, information about the preset point on the object, and information about the SOD between the preset point on the object and the X-ray radiator 1410.

When the user input unit 1460 receives the command regarding the alignment from the user, the driving controller 1430 may determine the location and rotation angle for aligning the X-ray radiator 1410 with the X-ray detector 1420 while maintaining the SOD. When the user input unit 1460 receives the command regarding the alignment from the user, the driver 1440 may move and rotate the X-ray radiator 1410 according to the location and the rotation angle determined by the driving controller 1430.

Figure 15A:
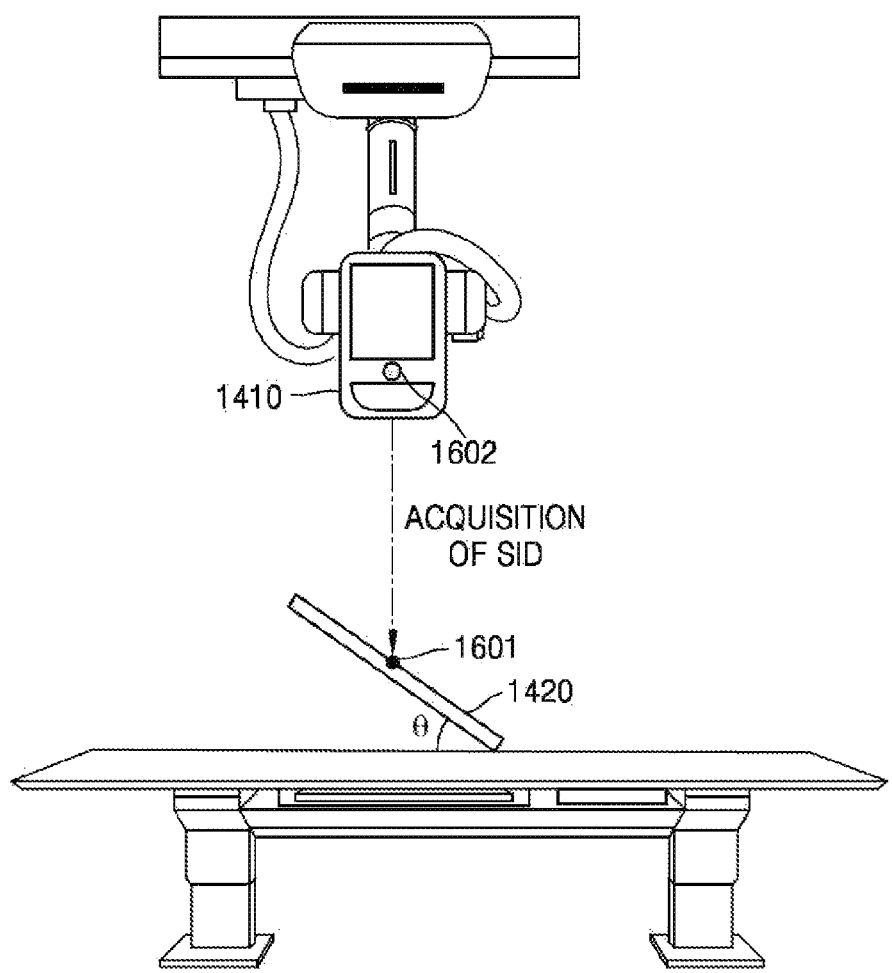
FIGS. 15A and 15B illustrate an exemplary embodiment in which an X-ray radiator is aligned with an X-ray detector while maintaining a Source to Image-receptor Distance (SID) therebetween.
Figure 15B:
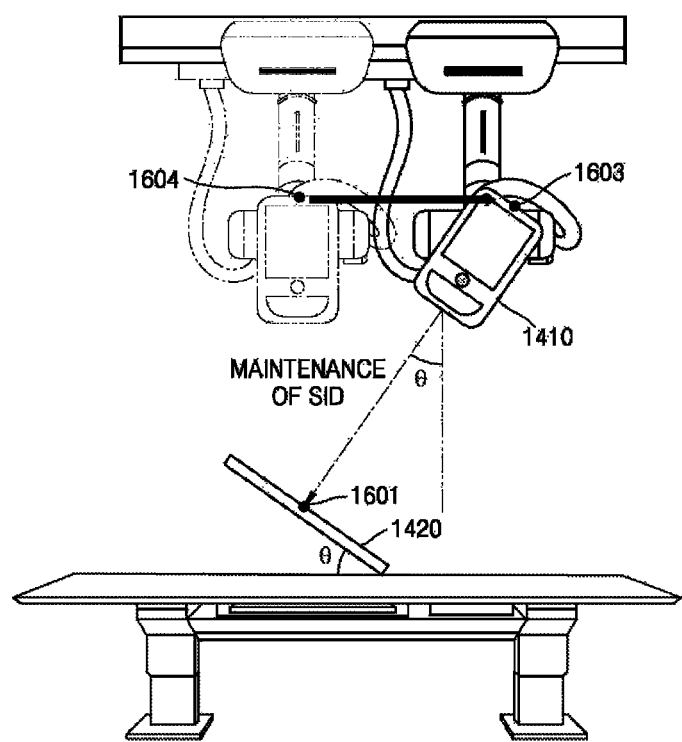

FIGS. 15A and 15B illustrate an exemplary embodiment in which the X-ray radiator 1410 is aligned with the X-ray detector 1420 while maintaining the SID therebetween.

Although not shown in FIGS. 15A and 15B, the X-ray apparatus 1400 may further include other components that may be included in the X-ray apparatus 1400, in addition to the X-ray radiator 1410 and the X-ray detector 1420.

The driving controller 1430 may acquire information about a preset point 1601 on the X-ray detector 1420. A user may move the X-ray radiator 1410 so that the X-ray radiator 1410 faces a point 1601 on the X-ray detector 1420 desired by the user, and the driving controller 1430 may set the point 1601 on the X-ray detector 1420 desired by the user to be the preset point 1601 on the X-ray detector 1420.

The user input unit 1460 may receive a command regarding alignment between the X-ray radiator 1410 and the X-ray detector 1420 from the user via a button 1602.

The driving controller 1430 may acquire information about an SID between the preset point 1601 on the X-ray detector 1420 and the X-ray radiator 1410. According to an exemplary embodiment, the driving controller 1430 may acquire the SID, based on the detector image acquired by the image acquirer 1450.

The driving controller 1430 may also acquire an angle θ at which the X-ray detector 1420 has been tilt, as the angle information.

The driving controller 1430 may determine the location and rotation angle for aligning the X-ray radiator 1410 with the X-ray detector 1420 while maintaining the SID, based on the acquired angle information, the acquired information about the preset point 1601, and the acquired information about the SID.

As shown in FIG. 15B, the driving controller 1430 may determine a location 1603 and a rotation angle θ for aligning the X-ray radiator 1410 with the X-ray detector 1420 while maintaining the SID. In FIGS. 15A and 15B, the X-ray radiator 1410 rotates by the angle θ from a direction in which the X-ray radiator 1410 perpendicularly faces a horizontal surface. However, exemplary embodiments are not limited thereto. In other words, when the X-ray radiator 1410 has already been rotated clockwise by φ, the driving controller 1430 may determine the rotation angle to be θ-φ, in order to align the X-ray radiator 1410 with the X-ray detector 1420.

The driver 1440 may move and rotate the X-ray radiator 1410 according to the location 1603 and the rotation angle θ determined by the driving controller 1430. In other words, the driver 1440 may move the X-ray radiator 1410 from a location 1604 to the location 1603, and rotate the X-ray radiator 1410 by the angle θ. Accordingly, the X-ray apparatus 1400 may align the X-ray radiator 1410 with the X-ray detector 1420 while maintaining the SID therebetween.

Figure 16A:
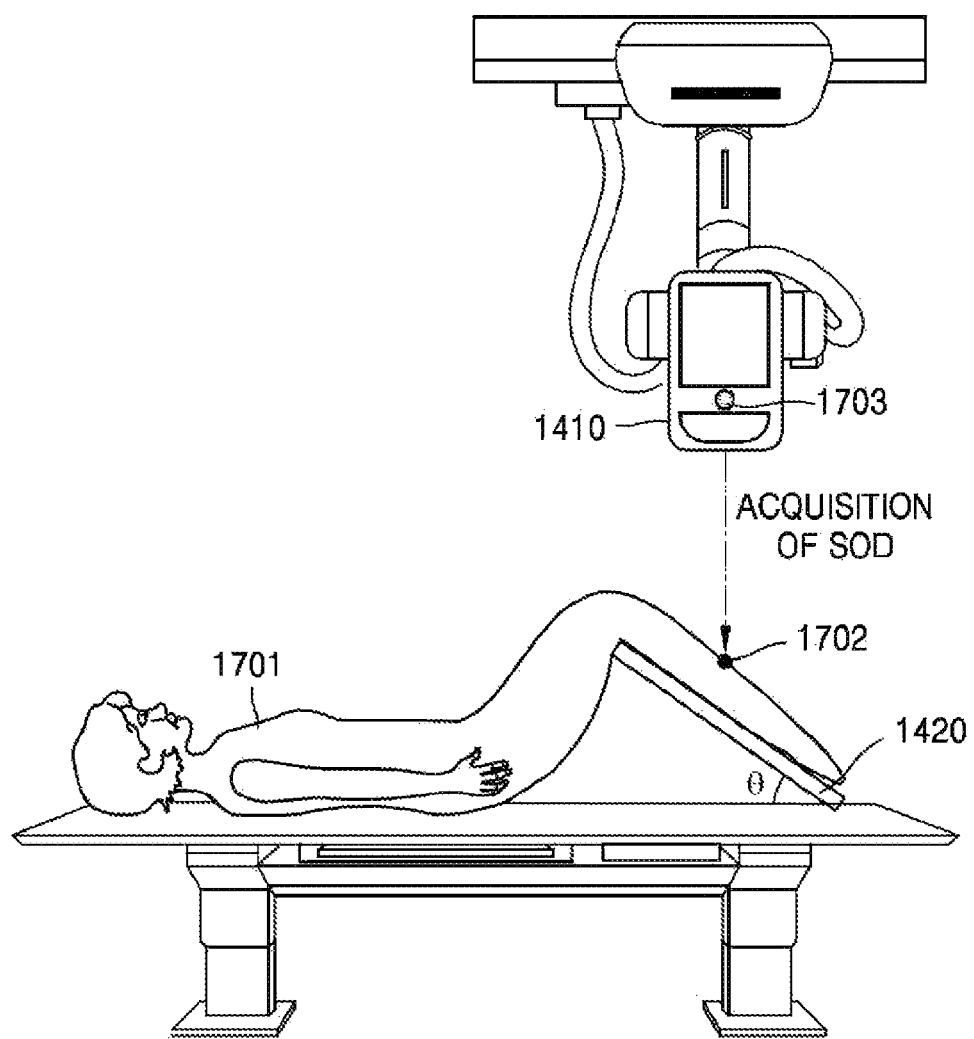
FIGS. 16A and 16B illustrate an exemplary embodiment in which an X-ray radiator is aligned with an X-ray detector while maintaining a Source to Object Distance (SOD) therebetween.
Figure 16B:
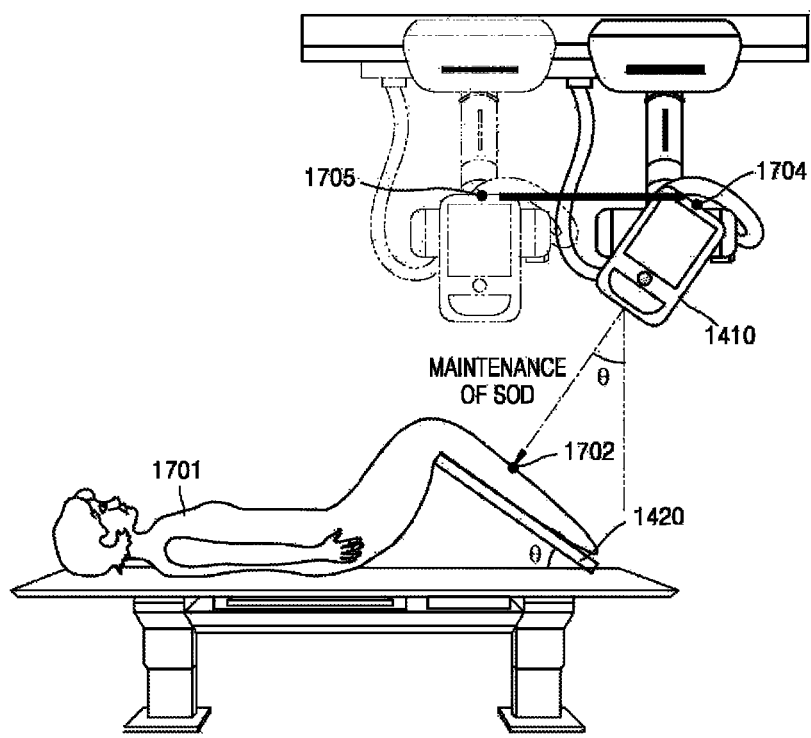

FIGS. 16A and 16B illustrate an exemplary embodiment in which the X-ray radiator 1410 is aligned with the X-ray detector 1420 while maintaining the SOD therebetween.

Although not shown in FIGS. 16A and 16B, the X-ray apparatus 1400 may further include other components that may be included in the X-ray apparatus 1400, in addition to the X-ray radiator 1410 and the X-ray detector 1420.

The driving controller 1430 may acquire information about a preset point 1702 on an object 1701. The object 1701 is a leg of a human in FIGS. 16A and 16B, but exemplary embodiments are not limited thereto. A user may move the X-ray radiator 1410 so that the X-ray radiator 1410 faces a point 1702 on the object 1701 desired by the user, and the driving controller 1430 may set the point 1702 on the object 1701 desired by the user to be the preset point 1702 on the object 1701.

The user input unit 1460 may receive a command regarding alignment between the X-ray radiator 1410 and the X-ray detector 1420 from the user via a button 1703.

The driving controller 1430 may acquire information about an SOD between the preset point 1702 on the object 1701 and the X-ray radiator 1410. According to an exemplary embodiment, the driving controller 1430 may acquire the SOD, based on the object image acquired by the image acquirer 1450.

The driving controller 1430 may also acquire an angle θ at which the X-ray detector 1420 has been tilt, as the angle information.

The driving controller 1430 may determine the location and rotation angle for aligning the X-ray radiator 1410 with the X-ray detector 1420 while maintaining the SOD, based on the acquired angle information, the acquired information about the preset point 1702, and the acquired information about the SOD.

As shown in FIG. 16B, the driving controller 1430 may determine a location 1704 and a rotation angle θ for aligning the X-ray radiator 1410 with the X-ray detector 1420 while maintaining the SOD. In FIGS. 16A and 16B, the X-ray radiator 1410 rotates by the angle θ from a direction in which the X-ray radiator 1410 perpendicularly faces a horizontal surface. However, exemplary embodiments are not limited thereto. In other words, when the X-ray radiator 1410 has already been rotated clockwise by φ, the driving controller 1430 may determine the rotation angle to be θ-φ, in order to align the X-ray radiator 1410 with the X-ray detector 1420.

The driver 1440 may move and rotate the X-ray radiator 1410 according to the location 1704 and the rotation angle θ determined by the driving controller 1430. In other words, the driver 1440 may rotate the X-ray radiator 1410 by the angle θ. The driver 1440 may move the X-ray radiator 1410 from a location 1705 to the location 1704, and the X-ray apparatus 1400 may align the X-ray radiator 1410 with the X-ray detector 1420 while maintaining the SOD therebetween.

Figure 17:
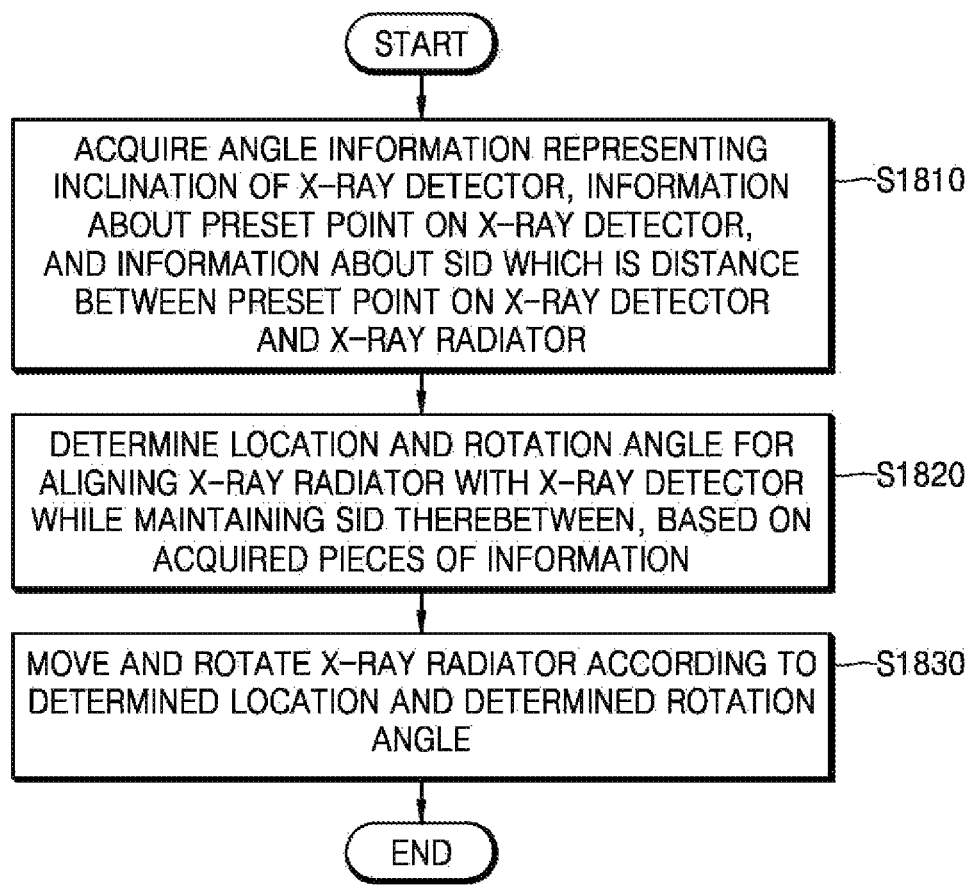
FIG. 17 is a flowchart of a method of operating an X-ray apparatus, according to an exemplary embodiment.

FIG. 17 is a flowchart of a method of operating the X-ray apparatuses 1300 and 1400, according to an exemplary embodiment.

The method of FIG. 17 may be performed by the X-ray apparatuses 1300 and 1400 of FIGS. 12 and 13, and a redundant description thereof will be omitted here.

In operation S1810, the X-ray apparatuses 1300 and 1400 may acquire angle information representing an inclination of an X-ray detector, information about a preset point on the X-ray detector, and information about an SID which is a distance between the preset point on the X-ray detector and the X-ray radiator.

The angle information representing the inclination of the X-ray detector may include an angle representing an inclination of an incidence surface of the X-ray detector. In other words, the angle information may include an angle between the incidence surface of the X-ray detector and a horizontal surface.

According to an exemplary embodiment, the X-ray apparatuses 1300 and 1400 may acquire the information about the preset point on the X-ray detector, based on a point on the X-ray detector that is viewed by the X-ray radiator. In more detail, when the X-ray radiator radiates light onto the X-ray detector via a radiation window including cross lines, the X-ray apparatuses 1300 and 1400 may set an intersection between the cross lines formed on the X-ray detector to be the preset point. Accordingly, a user may manipulate a direction of the X-ray radiator so that the X-ray radiator faces a point on the X-ray detector desired by the user, and the X-ray apparatuses 1300 and 1400 may set the point on the X-ray detector desired by the user to be the preset point on the X-ray detector 1320.

According to an exemplary embodiment, the X-ray apparatuses 1300 and 1400 may acquire information about an SID which is a distance between the preset point on the X-ray detector and the X-ray radiator, based on a user input. According to another exemplary embodiment, the X-ray apparatuses 1300 and 1400 may calculate the distance between the X-ray radiator and the preset point on the X-ray detector and acquire the calculated distance as information about the SID. For example, the X-ray apparatuses 1300 and 1400 may acquire the information about the SID, based on an image acquired by an image acquirer. As another example, the X-ray apparatuses 1300 and 1400 may acquire the information about the SID, by using a device which generates energy such as ultrasound waves, infrared, or RF and a device which receives energy reflected by the X-ray detector.

According to another exemplary embodiment, the X-ray apparatuses 1300 and 1400 may acquire angle information representing an inclination of the X-ray detector, information about a preset point on an object, and information about an SOD which is a distance between the preset point on the object and the X-ray radiator.

The X-ray apparatuses 1300 and 1400 may acquire the information about the preset point on the object, based on a point on the object that is viewed by the X-ray radiator. For example, a user may manipulate a direction of the X-ray radiator so that the X-ray radiator faces a point on the object desired by the user, and the X-ray apparatuses 1300 and 1400 may acquire information about the preset point on the object based on the point on the object desired by the user.

The X-ray apparatuses 1300 and 1400 may acquire information about an SOD which is a distance between the preset point on the object and the X-ray radiator, based on a user input. According to another exemplary embodiment, the X-ray apparatuses 1300 and 1400 may calculate the distance between the X-ray radiator and the preset point on object and acquire the calculated distance as information about the SOD.

In operation S1820, the X-ray apparatuses 1300 and 1400 may determine a location and a rotation angle for aligning the X-ray radiator with the X-ray detector while maintaining the SID therebetween, based on the acquired pieces of information.

In more detail, the X-ray apparatuses 1300 and 1400 may determine a rotation angle for aligning the X-ray radiator with the X-ray detector, based on the angle information of the X-ray detector, and may determine a location at which the X-ray radiator is to be positioned to maintain the SID from the X-ray detector, based on the information about the preset point on the X-ray detector and the information about the SID.

According to another exemplary embodiment, the X-ray apparatuses 1300 and 1400 may determine a location and a rotation angle for aligning the X-ray radiator with the X-ray detector while maintaining the SOD therebetween, based on the acquired pieces of information. In more detail, the X-ray apparatuses 1300 and 1400 may determine a rotation angle for aligning the X-ray radiator with the X-ray detector, based on the angle information of the X-ray detector, and may determine a location at which the X-ray radiator is to be positioned to maintain the SOD from the X-ray detector, based on the information about the preset point on the object and the information about the SOD.

In operation S1830, the X-ray apparatuses 1300 and 1400 may move and rotate the X-ray radiator according to the determined location and the determined rotation angle.

The X-ray apparatuses 1300 and 1400 may move and rotate the X-ray radiator according to the determined location and the determined rotation angle. In other words, the X-ray apparatuses 1300 and 1400 may move and rotate the X-ray radiator in order to align the X-ray radiator with the X-ray detector while maintaining the SID therebetween.

According to another exemplary embodiment, the X-ray apparatuses 1300 and 1400 may move and rotate the X-ray radiator according to the determined location and the determined rotation angle. In other words, the X-ray apparatuses 1300 and 1400 may move and rotate the X-ray radiator in order to align the X-ray radiator with the X-ray detector while maintaining the SOD therebetween.

Figure 18:
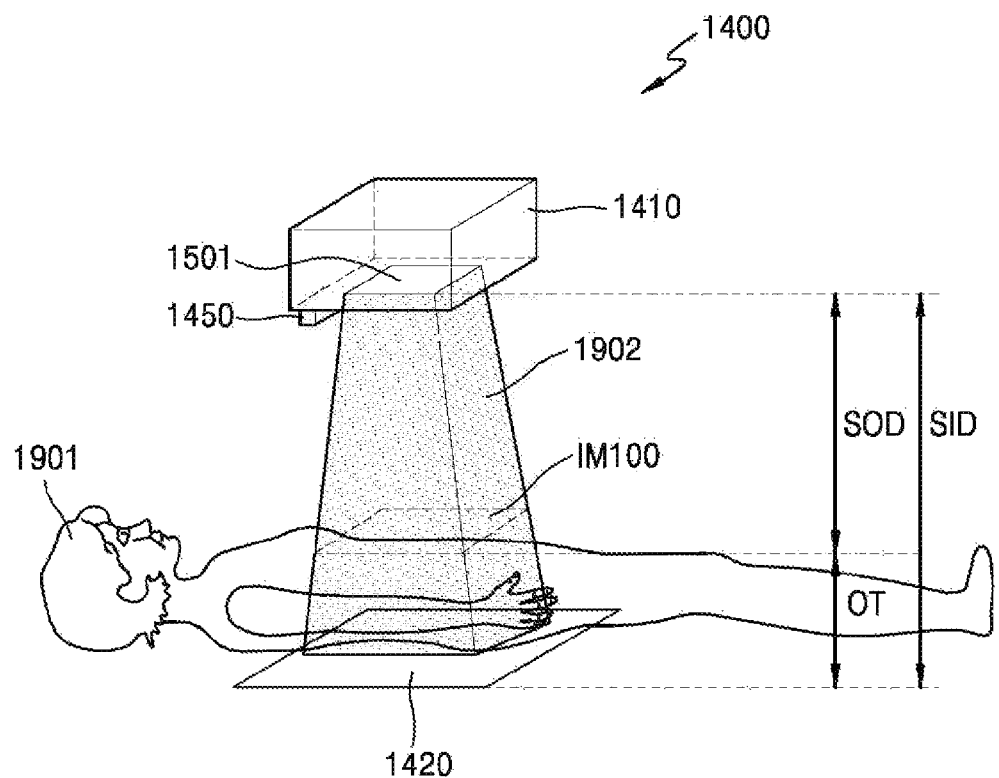
FIGS. 18, 19, and 20 illustrate an exemplary embodiment of acquiring an SOD by using an X-ray apparatus.

FIGS. 18-20 illustrate an exemplary embodiment of acquiring an SOD by using the X-ray apparatus 1400. Although not mentioned individually, the above description may be applied to several components included in the X-ray apparatus 1400 of FIG. 13. Components of FIG. 13 that are not illustrated in FIG. 18 may be included in the X-ray apparatus 1400 of FIG. 18. Accordingly, the X-ray apparatus 1400 of FIG. 18 may include the driving controller 1430 of FIG. 13, and the X-ray radiator 1410 of FIG. 18 may include the collimator 1414 including the lamp 1415 of FIG. 13, and the X-ray source 1412 of FIG. 13.

For convenience of explanation, in FIG. 18, when the X-ray detector 1420 is placed on a horizontal surface, an image of an object 1901 is captured via photography and an SOD is acquired. However, even when the X-ray detector 1420 is tilted, the image of the object 1901 may be equally captured via photography, and the SOD may be equally acquired.

Referring to FIGS. 13 and 18, when the lamp 1415 of the collimator 1414 is turned on, light from the lamp 1415 may be radiated via the radiation window 1501 of the collimator 1414. Due to a radiation area 1902 of the light from the lamp 1415, an image IM100 of the radiation window 1501 may be formed on the object 1901. The image IM100 of the radiation window 1501 formed on the object 1901 may be referred to as a radiation window image IM100 on the object 1901.

The image acquirer 1450 may acquire an object image by photographing the object 1901. Since the radiation window image IM100 is formed on the object 1901, the object image acquired by the image acquirer 1450 may include an image area for the radiation window image IM100.

FIG. 19 illustrates an exemplary embodiment of an object image 2001 acquired by the X-ray apparatus 1400 of FIG. 18.

Referring to FIGS. 18 and 19, the object image 2001 includes an image area 2002 for the radiation window image IM100 formed on the object 1901. Hereinafter, the image area 2002 for the radiation window image IM100 included in the object image 2001 is referred to as "a collimation area" or "a radiation field of a collimator" of the object image 2001. In other words, the collimation area 2002 is included in the object image 2001, and corresponds to the radiation area 1902 of light that is radiated from the lamp 1415 of the collimator 1414.

The object image 2001 may denote two-dimensional data comprised of respective pixel values of pixels which are discrete image elements. The pixel value may be at least one information from among brightness and color. The collimation area 2002 of the object image 2001 may be a group of pixels.

Referring back to FIGS. 13 and 19, the driving controller 1430 may detect the collimation area 2002 from the object image 2001. The driving controller 1430 may acquire the SOD based on a size of the detected collimation area 2002.

The driving controller 1430 may detect the collimation area 2002, based on brightness information of the object image 2001. The collimation area 2002 of the object image 2001 may be brighter than the other areas. In other words, the pixel values of the pixels included in the collimation area 2002 may have high brightness compared with those included in the other areas.

The driving controller 1430 may detect the collimation area 2002, based on the shape of the radiation window 1501 of the collimator 1414. The shape of the collimation area 2002 may vary depending on the shape of the radiation window 1501. For example, as shown in FIG. 14, when the radiating window 1501 is rectangular, the collimation area 2002 may be rectangular. When the radiation window 1501 includes cross lines as shown in FIG. 14, the collimation area 2002 may also include cross lines L1 and L2, as shown in FIG. 19. Accordingly, the driving controller 1430 may detect the collimation area 2002 by using a pattern recognition algorithm based on the shape of the radiation window 1501. For example, when the radiation window 1501 is rectangular, the driving controller 1430 may use a rectangular pattern recognition algorithm.

At this time, the driving controller 1430 may set a predetermine error range to the shape of the collimation area 2002 that is based on the shape of the radiation window 1501 of the collimator 1414. Due to curvature of the object 1901, the radiation window image IM100 as the image of the radiating window 1501 formed on the object 1901 may be somewhat distorted from the original shape of the radiating window 1501. Accordingly, the shape of the collimation area 2002 of the object image 1901 may also be distorted. Thus, the driving controller 1430 may set a predetermine error range to the shape of the collimation area 2002 in consideration of this distortion. For example, when the radiating window 1501 is rectangular, the collimation area 2002 may have a trapezoidal shape which is similar to a rectangle.

Alternatively, the driving controller 1430 may reduce the size of the radiation window 1501 via the shutter 1502 to reduce a distortion of the shape of the collimation area 2002. In this case, the size of the collimation area 2002 is also reduced within the object image 2001, and thus a distortion of the shape of the collimation area 2002 may be reduced. However, as the size of the collimation area 2002 decreases, the accuracy of the SOD obtained by the driving controller 1430 may decrease. Thus, the driving controller 1430 may adjust the size of the radiating window 2002, based on a trade-off with the accuracy of the SOD.

As such, the driving controller 1430 may detect the collimation area 2002, based on brightness information of the object image 2001 and the shape of the radiation window 1501, for example. The driving controller 1430 may acquire the SOD, based on the size of the detected collimation area 2002. The size of the collimation area 2002 may be the number of pixels included in the collimation area 2002.

Alternatively, the size of the collimation area 2002 may be the area of the collimation area 2002. The driving controller 1430 may detect the cross lines L1 and L2 of the object image 2001 corresponding to the cross lines of the collimation area 2002, and acquire the size of the collimation area 2002, based on the detected cross lines L1 and L2. The driving controller 1430 may detect the cross lines L1 and L2, based on brightness information of the object image 2001 and the shape of the radiation window 1501, for example. The driving controller 1430 may detect respective lengths of the cross lines L1 and L2. For example, the respective lengths of the cross lines L1 and L2 may be the number of pixels included in the cross line L1 and the number of pixels included in the cross line L2, respectively. The driving controller 1430 may acquire the size of the collimation area 2002 by multiplying the respective lengths of the cross lines L1 and L2 by each other.

Alternatively, the size of the collimation area 2002 may be estimated from one the respective lengths of the cross lines L1 and L2. The driving controller 1430 may acquire the size of the collimation area 2002, based on one of the respective lengths of the detected cross lines L1 and L2 of the radiation window 1501.

The driving controller 1430 may acquire the SOD, based on the size of the collimation area 2002. However, the above-described method is only an example of a method of acquiring the size of the collimation area 2002, and exemplary embodiments are not limited thereto.

The size of the collimation area 2002 in the object image 2001 varies depending on the SOD. Accordingly, when the driving controller 1430 acquires relationship information representing a relationship between the size of the collimation area 2002 and the SOD, the driving controller 1430 may acquire the SOD, based on the relationship information.

FIG. 20 is a graph of relationship information representing a relationship between the size of a collimation area and the SOD.

Referring to FIG. 20, the X axis is the SOD, and the Y axis is the size of the collimation area within an object image. As the SOD increases, the size of the collimation area decreases. According to perspective, as the SOD increases, the size of the collimation area of an object image captured via photography may decrease. Accordingly, when a size OA of the collimation area is acquired from the object image, the SOD may be acquired based on relationship information as shown in FIG. 20.

Referring back to FIG. 18, the driving controller 1430 of the X-ray apparatus 1400 may acquire the SOD, based on relationship information (for example, FIG. 20) representing a relationship between the size of the collimation area and the SOD. The driving controller 1430 may also acquire an object thickness OT which is a thickness of the object 1901, based on the SID and the SOD. The object thickness OT may be a difference between the SID and the SOD.

As such, according to some exemplary embodiments, the X-ray apparatus 1400 may automatically acquire an SOD which is a distance between the X-ray source 1412 and the object 1901, based on an object image obtained by photographing the object 1901. The X-ray apparatus 1400 may acquire the object thickness OT, based on an SID which is a distance between the X-ray source 1412 and the X-ray detector 1420 and the SOD. According to some exemplary embodiments, the X-ray apparatus 1400 may automatically acquire the SOD or the OT without using additional measurement tools such as a separate sensor or tapeline.

The driving controller 1430 may also acquire the SID, similar to acquiring the SOD.

The apparatuses described herein may comprise a processor, a memory for storing program data and executing it, a permanent storage unit such as a disk drive, a communications port for handling communications with external devices, and user interface devices, including a touch panel, keys, buttons, etc. When software modules or algorithms are involved, these software modules may be stored as program instructions or computer readable codes executable on a processor on a computer-readable medium. Examples of the computer readable recording medium include magnetic storage media (e.g., read-only memory (ROM), random-access memory (RAM), floppy disks, hard disks, etc.), and optical recording media (e.g., CD-ROMs, or Digital Versatile Discs (DVDs)). The computer readable recording medium can also be distributed over network coupled computer systems so that the computer readable code is stored and executed in a distributive manner. This media can be read by the computer, stored in the memory, and executed by the processor.

Exemplary embodiments may be described in terms of functional block components and various processing steps. Such functional blocks may be realized by any number of hardware and/or software components configured to perform the specified functions. For example, exemplary embodiments may employ various integrated circuit (IC) components, e.g., memory elements, processing elements, logic elements, look-up tables, and the like, which may carry out a variety of functions under the control of one or more microprocessors or other control devices. Similarly, where the elements are implemented using software programming or software elements, the exemplary embodiments described herein may be implemented with any programming or scripting language such as C, C++, Java, assembler language, or the like, with the various algorithms being implemented with any combination of data structures, objects, processes, routines or other programming elements. Functional aspects may be implemented in algorithms that are executed on one or more processors. Furthermore, the exemplary embodiments described herein could employ any number of conventional techniques for electronics configuration, signal processing and/or control, data processing and the like. The words "mechanism," "element," "means," and "configuration" are used broadly and are not limited to mechanical or physical exemplary embodiments, but can include software routines in conjunction with processors, etc.

The particular implementations shown and described herein are illustrative examples and are not intended to otherwise limit the scope of the exemplary embodiments in any way. For the sake of brevity, conventional electronics, control systems, software development and other functional aspects of the systems may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical apparatus.

The use of the terms "a" and "an" and "the" and similar referents in the context of describing the exemplary embodiments (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The exemplary embodiments are not limited to the described order of the steps. The use of any and all examples, or exemplary language (e.g., "such as") provided herein, is intended merely to better illuminate the exemplary embodiments and does not pose a limitation on the scope of the exemplary embodiments unless otherwise claimed. Numerous modifications and adaptations will be readily apparent to one of ordinary skill in the art without departing from the spirit and scope.

The exemplary embodiments should be considered in descriptive sense only and not for purposes of limitation. Descriptions of features or aspects within each exemplary embodiment should typically be considered as available for other similar features or aspects in other exemplary embodiments.

While the exemplary embodiments have been particularly shown and described, it will be understood by those of ordinary skill in the art that various changes in form and details may be made therein without departing from the spirit and scope of the exemplary embodiments as defined by the following claims.

What is claimed is:

1. An X-ray apparatus comprising:
an X-ray radiator configured to irradiate an X-ray in a radiation direction;
an X-ray detector comprising an incidence surface, the X-ray detector being configured to detect the X-ray radiated from the X-ray radiator to the incidence surface;
a controller configured to:
acquire first angle information representing an inclination of the X-ray detector,
acquire second angle information representing an angle by which the X-ray radiator is rotated from a reference position, and
determine a rotation angle of the X-ray radiator for aligning the X-ray radiator with the X-ray detector of the X-ray radiator based on the first angle information and the second angle information, and a rotation direction of the X-ray radiator based on a motion information corresponding to a motion of the X-ray detector such that a radiation direction of the X-ray radiator is perpendicular to the incidence surface of the X-ray detector; of the X-ray detector; and
a driver configured to rotate the X-ray radiator by the rotation angle in the rotation direction.

2. The X-ray apparatus of claim 1, wherein:
the controller is further configured to:
determine the rotation angle based on a difference between the first angle and the second angle, and
determine the rotation direction based on whether the X-ray detector rotates in a clockwise or counter-clockwise direction.

3. The X-ray apparatus of claim 1, further comprising an output unit having a screen, wherein the output unit is configured to display information on the screen representing that the X-ray radiator is aligned with the X-ray detector after the X-ray radiator is rotated by the rotation angle in the rotation direction.

4. The X-ray apparatus of claim 3, wherein the output unit is further configured to display the first angle information and the second angle information.

5. The X-ray apparatus of claim 1, further comprising a user input unit configured to receive a command regarding alignment of the X-ray radiator with the X-ray detector from a user, wherein the controller is further configured to determine the rotation angle and the rotation direction according to the command.

6. The X-ray apparatus of claim 1, wherein the controller is further configured to transmit the rotation angle and the rotation direction to the driver via a Controller Area Network (CAN).

7. A method of operating an X-ray apparatus, the method comprising:
acquiring first angle information representing an inclination of an X-ray detector,
acquiring second angle information representing an angle by which an X-ray radiator is rotated from a reference position;
acquiring motion information corresponding to a motion of the X-ray detector;
determining a rotation angle and a rotation direction of the X-ray radiator for aligning the X-ray radiator with the X-ray detector based on the first angle information, the second angle information, and the motion information; and
rotating the X-ray radiator by the rotation angle in the rotation direction.

8. The method of claim 7, wherein
the determining comprises:
determining the rotation angle based on a difference between the first angle and the second angle; and
determining the rotation direction based on whether the X-ray detectors in a clockwise or counterclockwise direction.

9. An X-ray apparatus comprising:
an X-ray radiator configured to irradiate an X-ray in a radiation direction:
an X-ray detector comprimising an incidence surface, the X-ray detector being configured to detect the X-ray radiated from the X-ray radiator to the incidence surface:
a controller configured to:
acquire information comprising information about a preset point on an object located between the X-ray radiator and the X-ray detector, and information about a Source to Object Distance (SOD), wherein the SOD is a distance between the preset point on the object and the X-ray radiator, and
determine a location and a rotation angle for aligning the X-ray radiator with the X-ray detector with the SOD being maintained, such that the radiation direction is perpendicular to the incidence surface, based on the acquired information, and
a driver configured to move the X-ray radiator according to the location and the rotation angle.

10. A method of operating an X-ray apparatus, the method comprising:
acquiring information comprising:
angle information representing an inclination of an X-ray detector,
motion information corresponding to a motion of the X-ray detector;
information about a preset point on the X-ray detector, and
information about an SID, wherein the SID is a distance between the preset point on the X-ray detector and an X-ray radiator;
determining a location and a rotation angle for aligning the X-ray radiator with the X-ray detector with the SID being maintained, based on the acquired information; and moving the X-ray radiator according to the location and the rotation angle determined to align the X-ray radiator with the X-ray detector with the SID being maintained.

11. An X-ray apparatus comprising:
an X-ray radiator configured to irradiate an X-ray in a radiation direction;
an X-ray detector comprising an incidence surface, the X-ray detector being configured to detect the X-ray radiated from the X-ray radiator to the incidence surface;
a controller configured to:
acquire information, comprising angle information representing an inclination of the X-ray detector, information about a preset point on the X-ray detector, and information about a Source to Image-receptor Distance (SID), wherein the SID is a distance between the preset point on the X-ray detector and the X-ray radiator, and
determine a location and a rotation angle of the X-ray radiator for aligning the X-ray radiator with the X-ray detector with the SID being maintained, such that the radiation direction is perpendicular to the incidence surface, based on the acquired information; and
a driver configured to move the X-ray radiator according to the location and the rotation angle.

12. The X-ray apparatus of claim 11, further comprising an image acquirer configured to acquire an image of a marker displayed on the X-ray detector wherein the image of the marker is generated by light from a collimator.

13. The X-ray apparatus of claim 12, wherein the controller is further configured to acquire information about the SID based on the image of the marker.

14. The X-ray apparatus of claim 12, wherein the marker comprises an intersection between cross-lines of the collimator that is marked on the X-ray detector by light of a laser pointer included in the collimator.

15. The X-ray apparatus of claim 12, wherein the marker comprises an intersection between cross-lines of the collimator that is marked on the X-ray detector by light of a lamp when the lamp of the collimator is turned on.

16. The X-ray apparatus of claim 11, further comprising a user input unit configured to receive a command regarding maintenance of the SID between the X-ray radiator and the X-ray detector and alignment of the X-ray radiator and the X-ray detector from a user, wherein the controller is further configured to determine the rotation angle according to the command.

17. The method of claim 16, further comprising:
acquiring information comprising:
information about a preset point on an object located between the X-ray radiator and the X-ray detector, and
information about an SOD which is a distance between the preset point on the object and the X-ray radiator;
determining a location and a rotation angle for aligning the X-ray radiator with the X-ray detector while maintaining the SOD, based on the acquired information; and
moving and rotating the X-ray radiator according to the location and the rotation angle determined align the X-ray radiator with the X-ray detector while maintaining the SOD.

18. The X-ray apparatus of claim 1, the motion information comprises a rotation direction of the X-ray detector.

19. The method of claim 7, wherein the motion information comprises a rotation direction of the X-ray detector.

* * * * *